United States Patent
Zhang et al.

(10) Patent No.: US 10,155,028 B2
(45) Date of Patent: Dec. 18, 2018

(54) METHOD FOR PROPHYLAXIS AND/OR TREATMENT OF ERBB2 POSITIVE CANCERS

(71) Applicant: Health Research, Inc., Buffalo, NY (US)

(72) Inventors: Yuesheng Zhang, Orchard Park, NY (US); Lu Yang, Buffalo, NY (US); Yun Li, Orchard Park, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 14/913,515

(22) PCT Filed: Aug. 20, 2014

(86) PCT No.: PCT/US2014/051789
§ 371 (c)(1),
(2) Date: Feb. 22, 2016

(87) PCT Pub. No.: WO2015/031119
PCT Pub. Date: Mar. 5, 2015

(65) Prior Publication Data
US 2016/0199462 A1 Jul. 14, 2016

Related U.S. Application Data

(60) Provisional application No. 61/870,054, filed on Aug. 26, 2013.

(51) Int. Cl.
| | |
|---|---|
| *A61K 39/00* | (2006.01) |
| *A61K 38/48* | (2006.01) |
| *A61K 45/06* | (2006.01) |
| *C12N 9/48* | (2006.01) |

(52) U.S. Cl.
CPC .......... *A61K 38/4813* (2013.01); *A61K 39/00* (2013.01); *A61K 45/06* (2013.01); *C12N 9/485* (2013.01); *C07K 2319/21* (2013.01); *C07K 2319/30* (2013.01); *C12Y 304/13009* (2013.01)

(58) Field of Classification Search
None
See application file for complete search history.

(56) References Cited

U.S. PATENT DOCUMENTS

| | | |
|---|---|---|
| 6,812,339 B1 | 11/2004 | Venter et al. |
| 2002/0103133 A1* | 8/2002 | Copeland ............. C07K 7/06 514/19.4 |
| 2006/0134088 A1 | 6/2006 | Ammannati |
| 2006/0177448 A1 | 8/2006 | Carey |
| 2010/0173978 A1 | 7/2010 | D'Alessio |
| 2013/0165389 A1 | 6/2013 | Schellenberger et al. |

FOREIGN PATENT DOCUMENTS

| | | | |
|---|---|---|---|
| WO | WO-2004104595 A2 * | 12/2004 | ........... G01N 33/573 |
| WO | 2007110767 | 10/2007 | |

OTHER PUBLICATIONS

Yan et al, JBC, 288:2365-2375, 2012.*
Lima et al, Biosci Rep, online published Jul. 26, 2013 (Year: 2013).*
Azemar et al., Regression of Cutaneous Tumor Lesions in Patients Intratumorally Injected with a Recombinant Single-chain Antibody-toxin Targeted to ErbB2/HER2, Breast Cancer Research and Treatment, vol. 82, No. 3, pp. 155-164. Dec. 1, 2003.
Yang et al., Identification of prolidase as a high affinity ligand of the ErbB2 receptor and its regulation of ErbB2 signaling and cell growth, Cell Death and Disease, vol. 5, No. 5, p. e1211. May 8, 2014.
Yang et al., Inhibition of ERBB2-overexpressing Tumors by Recombinant Human Prolidase and Its Enzymatically Inactive Mutant, Ebiomedicine, vol. 2, No. 5, pp. 396-405. May 1, 2015.
Yang, L., et al., Prolidase Directly Binds and Activates Epidermal Growth Factor Receptor and Stimulates Downstream Signaling; Journal of Biological Chemistry, Dec. 4, 2012, vol. 288, No. 4, pp. 2365-2375.
Wu, Y., et al., A Meta-Analysis of Genome-Wide Association Studies for Adiponectin Levels in East Asians Identifies a Novel Locus Near WDR11-FGFR2: *Homo sampiens* peptidase D (PEPD), Transcript Variant 1, mRNA, NCBI Reference Sequence: MN_000285. 3, Hum. Mol. Genet., May 17, 2014, vol. 23, No. 4, pp. 1108-1119.

* cited by examiner

*Primary Examiner* — Lei Yao
(74) *Attorney, Agent, or Firm* — Hodgson Russ LLP

(57) ABSTRACT

Provided are compositions and methods for prophylaxis and/or therapy of ErbB2-positive cancer. The compositions include pharmaceutical preparations that contain isolated or recombinant or modified peptidase D (PEPD) proteins. The methods include prophylaxis and/or therapy of ErbB2-positive cancer by administering a PEPD to an individual who has or is at risk for developing ErbB2-positive cancer.

6 Claims, 19 Drawing Sheets

Specification includes a Sequence Listing.

SEQUENCE LISTING

<160> NUMBER OF SEQ ID NOS: 13

<210> SEQ ID NO 1
<211> LENGTH: 493
<212> TYPE: PRT
<213> ORGANISM: Human

<400> SEQUENCE: 1

```
Met Ala Ala Ala Thr Gly Pro Ser Phe Trp Leu Gly Asn Glu Thr Leu
1               5                   10                  15

Lys Val Pro Leu Ala Leu Phe Ala Leu Asn Arg Gln Arg Leu Cys Glu
            20                  25                  30

Arg Leu Arg Lys Asn Pro Ala Val Gln Ala Gly Ser Ile Val Val Leu
        35                  40                  45

Gln Gly Gly Glu Glu Thr Gln Arg Tyr Cys Thr Asp Thr Gly Val Leu
    50                  55                  60

Phe Leu Gln Glu Ser Phe Phe His Trp Ala Phe Gly Val Thr Glu Pro
65                  70                  75                  80

Gly Cys Tyr Gly Val Ile Asp Val Asp Thr Gly Lys Ser Thr Leu Phe
                85                  90                  95

Val Pro Arg Leu Pro Ala Ser His Ala Thr Trp Met Gly Lys Ile His
            100                 105                 110

Ser Lys Glu His Phe Lys Glu Lys Tyr Ala Val Asp Asp Val Gln Tyr
        115                 120                 125

Val Asp Glu Ile Ala Ser Val Leu Thr Ser Gln Lys Pro Ser Val Leu
    130                 135                 140

Leu Thr Leu Arg Gly Val Asn Thr Asp Ser Gly Ser Val Cys Arg Glu
145                 150                 155                 160

Ala Ser Phe Asp Gly Ile Ser Lys Phe Glu Val Asn Asn Thr Ile Leu
                165                 170                 175

His Pro Glu Ile Val Glu Ser Arg Val Phe Lys Thr Asp Met Glu Leu
            180                 185                 190

Glu Val Leu Arg Tyr Thr Asn Lys Ile Ser Ser Glu Ala His Arg Glu
        195                 200                 205

Val Met Lys Ala Val Lys Val Gly Met Lys Glu Tyr Gly Leu Glu Ser
    210                 215                 220

Leu Phe Glu His Tyr Cys Tyr Ser Arg Gly Gly Met Arg His Ser Ser
```

```
                225                 230                 235                 240
        Tyr Thr Cys Ile Cys Gly Ser Gly Glu Asn Ser Ala Val Leu His Tyr
                        245                 250                 255

Gly His Ala Gly Ala Pro Asn Asp Arg Thr Ile Gln Asn Gly Asp Met
                        260                 265                 270

Cys Leu Phe Asp Met Gly Gly Glu Tyr Tyr Ser Val Ala Ser Asp Ile
                        275                 280                 285

Thr Cys Ser Phe Pro Arg Asn Gly Lys Phe Thr Ala Asp Gln Lys Ala
                        290                 295                 300

Val Tyr Glu Ala Val Leu Leu Ser Ser Arg Ala Val Met Gly Ala Met
        305                 310                 315                 320

Lys Pro Gly Asp Trp Trp Pro Asp Ile Asp Arg Leu Ala Asp Arg Ile
                        325                 330                 335

His Leu Glu Glu Leu Ala His Met Gly Ile Leu Ser Gly Ser Val Asp
                        340                 345                 350

Ala Met Val Gln Ala His Leu Gly Ala Val Phe Met Pro His Gly Leu
                        355                 360                 365

Gly His Phe Leu Gly Ile Asp Val His Asp Val Gly Gly Tyr Pro Glu
                        370                 375                 380

Gly Val Glu Arg Ile Asp Glu Pro Gly Leu Arg Ser Leu Arg Thr Ala
        385                 390                 395                 400

Arg His Leu Gln Pro Gly Met Val Leu Thr Val Glu Pro Gly Ile Tyr
                        405                 410                 415

Phe Ile Asp His Leu Leu Asp Glu Ala Leu Ala Asp Pro Ala Arg Ala
                        420                 425                 430

Ser Phe Leu Asn Arg Glu Val Leu Gln Arg Phe Arg Gly Phe Gly Gly
                        435                 440                 445

Val Arg Ile Glu Glu Asp Val Val Ile Asp Ser Gly Ile Glu Leu
                        450                 455                 460

Leu Thr Cys Val Pro Arg Thr Val Glu Glu Ile Glu Ala Cys Met Ala
        465                 470                 475                 480

Gly Cys Asp Lys Ala Phe Thr Pro Phe Ser Gly Pro Lys
                        485                 490

<210> SEQ ID NO 2
<211> LENGTH: 21
<212> TYPE: DNA
<213> ORGANISM: artificial sequence
<220> FEATURE:
<223> OTHER INFORMATION: primer

<400> SEQUENCE: 2
aatacgactc actatagggc g                                              21

<210> SEQ ID NO 3
<211> LENGTH: 17
<212> TYPE: DNA
<213> ORGANISM: artificial sequence
<220> FEATURE:
<223> OTHER INFORMATION: primer

<400> SEQUENCE: 3
cttggggcca gagaagg                                                   17

<210> SEQ ID NO 4
<211> LENGTH: 36
<212> TYPE: DNA
<213> ORGANISM: artificial sequence
```

```
<220> FEATURE:
<223> OTHER INFORMATION: primer

<400> SEQUENCE: 4
ataagaatgc ggccgcagct gagattcccc tccatt                          36

<210> SEQ ID NO 5
<211> LENGTH: 36
<212> TYPE: DNA
<213> ORGANISM: artificial sequence
<220> FEATURE:
<223> OTHER INFORMATION: primer

<400> SEQUENCE: 5
atagtttagc ggccgccttg atgccagcag aagtca                          36

<210> SEQ ID NO 6
<211> LENGTH: 21
<212> TYPE: DNA
<213> ORGANISM: artificial sequence
<220> FEATURE:
<223> OTHER INFORMATION: primer

<400> SEQUENCE: 6
caaatgggcg gtaggcgtgt a                                          21

<210> SEQ ID NO 7
<211> LENGTH: 24
<212> TYPE: DNA
<213> ORGANISM: artificial sequence
<220> FEATURE:
<223> OTHER INFORMATION: primer

<400> SEQUENCE: 7
attggtgggc aggtaggtga gttc                                       24

<210> SEQ ID NO 8
<211> LENGTH: 23
<212> TYPE: DNA
<213> ORGANISM: artificial sequence
<220> FEATURE:
<223> OTHER INFORMATION: primer

<400> SEQUENCE: 8
ctgtttgccg tgccaccctg agt                                        23

<210> SEQ ID NO 9
<211> LENGTH: 24
<212> TYPE: DNA
<213> ORGANISM: artificial sequence
<220> FEATURE:
<223> OTHER INFORMATION: primer

<400> SEQUENCE: 9
cttctgctgc cgtcgcttga tgag                                       24

<210> SEQ ID NO 10
<211> LENGTH: 19
<212> TYPE: DNA
<213> ORGANISM: artificial sequence
<220> FEATURE:
<223> OTHER INFORMATION: primer

<400> SEQUENCE: 10
ccagggctgc ttttaactc                                             19
```

```
<210> SEQ ID NO 11
<211> LENGTH: 18
<212> TYPE: DNA
<213> ORGANISM: artificial sequence
<220> FEATURE:
<223> OTHER INFORMATION: primer

<400> SEQUENCE: 11 gctccccct gcaaatga                                                    18

<210> SEQ ID NO 12
<211> LENGTH: 20
<212> TYPE: DNA
<213> ORGANISM: artificial sequence
<220> FEATURE:
<223> OTHER INFORMATION: primer

<400> SEQUENCE: 12
tggaatctac tggcgtcttc                                                 20

<210> SEQ ID NO 13
<211> LENGTH: 20
<212> TYPE: DNA
<213> ORGANISM: artificial sequence
<220> FEATURE:
<223> OTHER INFORMATION: primer

<400> SEQUENCE: 13
caccaccttc ttgatgtcct                                                 20
```

METHOD FOR PROPHYLAXIS AND/OR TREATMENT OF ERBB2 POSITIVE CANCERS

CROSS REFERENCE TO RELATED APPLICATIONS

This application claims priority to U.S. application No. 61/870,054, filed on Aug. 26, 2013, the disclosure of which is incorporated herein by reference.

STATEMENT REGARDING FEDERALLY SPONSORED RESEARCH

This invention was made with government support under contract nos. R01CA120533, R01CA24627 and R01CA164574 awarded by the National Cancer Institute. The government has certain rights in the invention.

FIELD OF THE DISCLOSURE

The present invention relates generally to the field of human health, and in particular to methods for the prophylaxis and treatment of cancers and/or other conditions that are positively correlated with the expression of ErbB2.

BACKGROUND OF THE INVENTION

ErbB2, also known as v-erb-b2 avian erythroblastic leukemia viral oncogene homolog 2, Her2, Neu, CD340, proto-oncogene C-ErbB2, is a member of the extensively studied ErbB family of plasma membrane-bound receptor tyrosine kinases, which also includes ErbB1, ErbB3 and ErbB4 (also known as EGFR/Her1, Her3 and Her4, respectively). These receptors have been shown to play critical roles in embryonic development, normal physiology and the development of various diseases. All four ErbB receptors contain an extracellular domain (ECD), a transmembrane domain and an intracellular domain that interacts with signaling molecules. Ligand binding to the ECDs of these receptors leads to homo- or hetero-dimerization, followed by the activation of the intrinsic protein tyrosine kinase and tyrosine autophosphorylation in the intracellular domain, and recruitment and activation of signaling proteins to these sites. Notably, ErbB3 is kinase-impaired and requires heterodimerization for activation. To date, while multiple ligands have been identified for ErbB1, ErbB3 and ErbB4, no ligand for ErbB2 has been found, ever since its discovery nearly 30 years ago (Coussens et al. *Science* 1985; 230: 1132-1139; Schechter et al. Science 1985; 229: 976-978). However, ErbB2 is a preferred dimerization partner for other ligand-bound ErbBs.

ErbB2 is best known for its involvement in human breast cancer. ErbB2 gene amplification occurs in 20-30% of breast cancer and is significantly correlated with ErbB2 protein expression in the cancer tissues. ErbB2 gene amplification or protein overexpression is a strong predictor of poor disease prognosis. ErbB2-targeted therapies, particularly humanized monoclonal antibody trastuzumab in combination with chemotherapy, show considerable clinical efficacy. However, many ErbB2-positive cancers show de novo resistance or acquired resistance to such a therapy. Thus, there is an ongoing and unmet need to identify a ligand of ErbB2 and to develop therapeutic approaches based at least in part upon such a ligand. The present disclosure meets these needs.

SUMMARY OF THE DISCLOSURE

The present disclosure provides compositions and methods useful for prophylaxis and/or therapy of ErbB2-positive cancers. The compositions and methods relate to the present discovery that prolidase is a ligand of the ErbB2 receptor. Further, this disclosure is believed to be the first description of any ErbB2 ligand.

Prolidase, also known as peptidase D (PEPD), Xaa-Pro dipeptidase or proline dipeptidase, or imidodipeptidase, is a protease which hydrolyzes dipeptides with proline or hydroxyproline at the carboxy terminus. PEPD is a ubiquitously expressed cytosolic protein and exists as a homodimer (monomeric molecular weight of human PEPD: 54 kD; 493 amino acids as shown in SEQ ID NO:1, which provides the amino acid sequence of human prolidase.). In embodiments, the PEPD that is used for the compositions and methods of the instant disclosure is a mammalian PEPD. In one embodiment, the PEPD is human PEPD. In embodiments, the PEPD can be enzymatically active or have reduced or have no detectable enzymatic activity.

The compositions comprise pharmaceutical preparations which contain an isolated and/or purified PEPD or recombinant and/or modified PEPD, and can further comprise additional agents, such as a coagulation inhibitor. In embodiments the PEPD is modified. In embodiments, the PEPD is a component of a fusion protein. In embodiments, the fusion protein comprises the PEPD and an amino acid sequence useful for purification of recombinantly produced PEPD.

The methods comprise administering to an individual in need of prophylaxis and/or therapy of an ErbB2-positive cancer a composition comprising a PEPD of this disclosure, and can further comprise administering to the individual a coagulation inhibitor. Also provided are methods for identifying individuals in need of treatment with PEPD formulations, and methods for generating a treatment protocol for such individuals.

In embodiments the disclosure further provides products comprising pharmaceutical preparations which contain an isolated and/or purified PEPD or recombinant PEPD, and which can also contain printed material describing use of the preparations for prophylaxis and/or therapy of ErbB2-positive cancers. In embodiments, the products also contain a coagulation inhibitor. In non-limiting embodiments, the ErbB2-positive cancers are breast, ovarian, stomach, or aggressive forms of uterine cancer, such as uterine serous endometrial carcinoma. In embodiments, ErbB2-positive cancer cells are cancer cells which overexpress ErbB2 or carry a higher copy number of the ERBB2 gene relative to a non-cancer cell. In embodiments, ErbB2-positive cancer cells are cells which express more ErbB2 than a reference, such as a cell of the same type that is not cancerous.

BRIEF DESCRIPTION OF THE FIGURES

FIG. 16. Data showing the effects of PEPD and coagulation inhibitor EP in vivo. CHO-K1 cells were inoculated subcutaneously to the flanks of female athymic nude mice (6-7 weeks of age) at $1 \times 10^6$ cells per site in a small volume of PBS; Matrigel mix. Starting 4 days after cell inoculation, the mice were treated with EP at 2.5 mg/kg by intraperitoneal injection once daily. Three days later (day 7 after cell inoculation), when the tumor volume reached approximately 26 mm$^3$, the mice were also treated with vehicle or PEPD at 0.2 mg/kg by intraperitoneal injection, which was given three times per week (Monday, Wednesday, Friday). On the days when both EP and PEPD/vehicle were given, PEPD/vehicle was given 1 h after EP. Tumor volume was measured three times per week (Monday, Wednesday, Friday). The mice were killed 24 h after the last treatment which was given on day 21 after cell inoculation (a total of 7 PEPD treatments), and blood samples were collected from the mice for measurement of plasma level of PEPD. (a) Each value is a mean±SEM (n=8-11). (b) Each value is mean±SD (n=3). This shows that PEPD does not target tumors without ErbB2 overexpression. Notably, these tumor cells do not express ErbB1, ErbB3 or ErbB4, as shown in FIG. 8a.

DESCRIPTION OF THE DISCLOSURE

The present disclosure is based at least in part on our discoveries that PEPD is a ligand of the ErbB2 receptor and that it can be used for inhibiting the growth of ErbB2-positive cancers. In particular, and without intending to be constrained by any particular theory, we demonstrate in the present disclosure that PEPD is an ErbB2 ligand which binds to subdomain 3 of the ErbB2 extracellular domain. PEPD binds to ErbB2 as a homodimer, with each subunit apparently binding to one ErbB2 monomer. When PEPD binds to pre-existing ErbB2 dimers, it rapidly silences the ErbB2-Src/CK2-PTEN-AKT signaling system. PEPD also binds to ErbB2 monomers, causing ErbB2 dimerization and tyrosine phosphorylation. However, ErbB2 activation by PEPD is apparently insignificant, because PEPD soon causes profound ErbB2 depletion due to ErbB2 internalization and degradation and PEPD selectively inhibits the growth of cells overexpressing ErbB2. It is also believed from data presented herein that PEPD strikes ErbB2 only when it is present in the extracellular space and does not involve its enzymatic activity. Thus, the present disclosure includes but is not limited to the revelations that PEPD is a ligand of the ErbB2 receptor but suppresses ErbB2 signaling; the enzymatic activity of PEPD is not involved in ErbB2 targeting; PEPD acts on ErbB2 only when it is present in the extracellular space; and PEPD selectively inhibits cells overexpressing ErbB2. Data presented herein demonstrate that PEPD and an enzymatically inactive derivative thereof have effective anti-Erb2+ cancer effects in clinically relevant animal modes. In particular, data presented herein demonstrates PEPD and an enzymatically inactive variant thereof specifically targets tumors overexpressing ErbB2, and suppression of the Erb2+ tumors is confirmed in an orthotopic breast tumor model. Moreover, data presented herein demonstrate that compositions and methods of this disclosure are effective in preventing recurrence of at least some Erb2+ tumors after cessation of treatment with the PEPD formulations.

The amino acid sequence of ErbB2 is provided in GenBank accession no. NM_004448.2. While variants in ErbB2 are known in the art, it is expected that the present method will function with any ErbB2 variant, provided that the erbB2 variant has an extracellular domain. The extracellular domain is known in the art and comprises amino acid number 23-652 in the primary amino acid sequence in the GenBank accession no. mentioned above.

Figure 6:
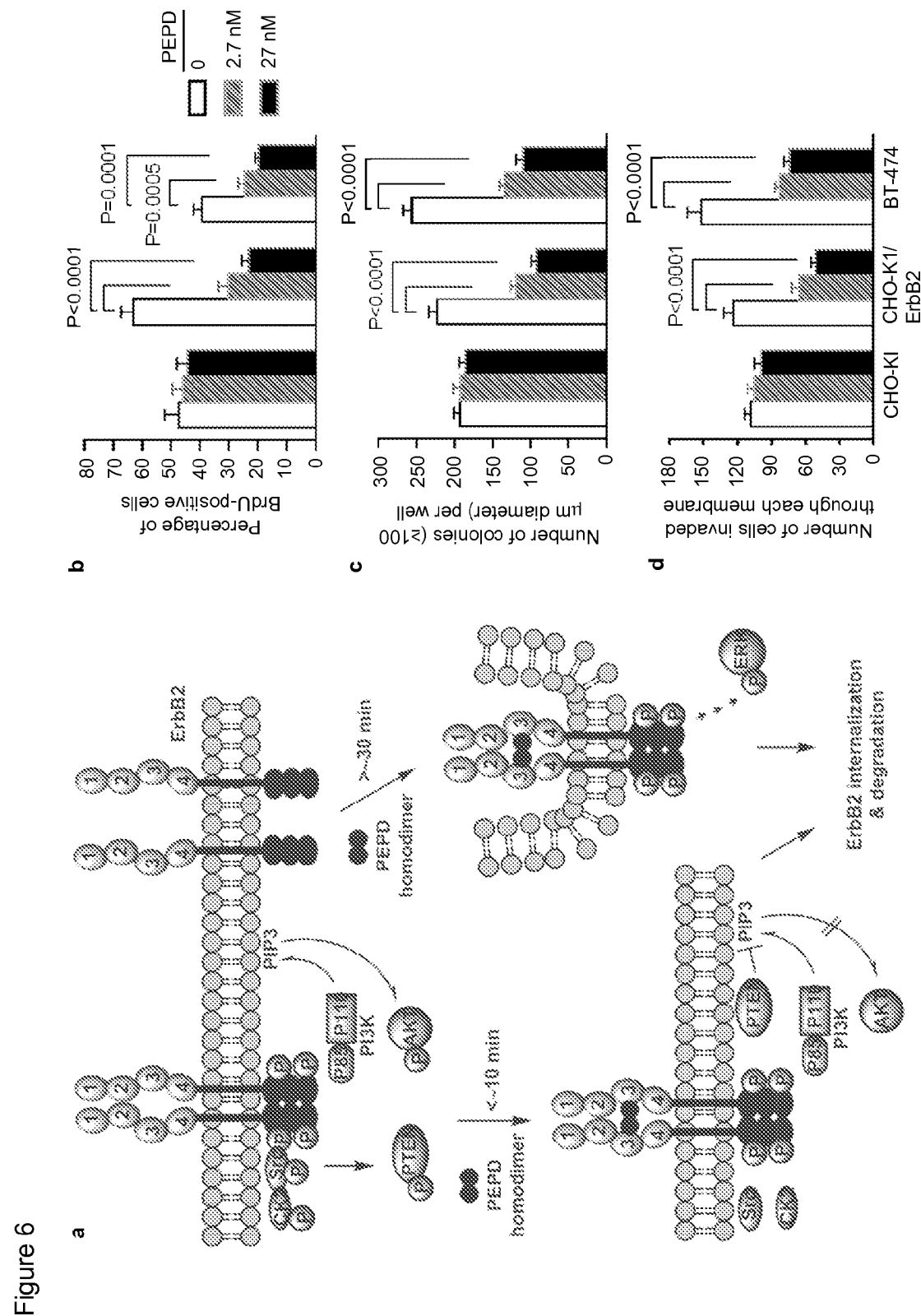
FIG. 6. Graphic showing paradigm of ErbB2 modulation by PEPD, and data showing selective inhibition of cells overexpressing ErbB2 by PEPD. (a) Both monomers and tyrosine-phosphorylated dimers exist in cells overexpressing ErbB2. PEPD binds to ErbB2 as a homodimer; each PEPD subunit binds to one ErbB2 ECD subdomain 3. PEPD rapidly binds to ErbB2 dimers, silencing ErbB2-Src signaling by causing Src disassociation from ErbB2. PEPD binds to ErbB2 monomers somewhat slowly but causes ErbB2 dimerization and phosphorylation, leading to activation of downstream signaling. PEPD also causes strong and persistent ErbB2 depletion resulting from PEPD-induced ErbB2 internalization and degradation. (b) Cells growing in 6-well plates were treated with vehicle or PEPD for 48 h and then measured for DNA synthesis by BrdU incorporation. (c) Cells growing in soft agar in 6-well plates were treated with vehicle or PEPD for 21 days (with medium change every 3-4 days) and then examined for colony formation. (d) Cells growing in invasion chambers were treated with vehicle or PEPD for 48 hours; cells that invaded through a Matrigel membrane were counted. Error bars in b-d indicate SD (n=3).

In more detail, it will be apparent from the instant disclosure and the Examples presented herein that the effect of PEPD on ErbB2 signaling represents a novel ligand-induced ErbB2 signaling as well as a novel PEPD function. A non-limiting, graphical illustration of this relationship is depicted in FIG. 6 which, without intending to be constrained by theory, demonstrates how selective inhibition of cells overexpressing ErbB2 by PEPD could exhibit therapeutic utility of PEPD against ErbB2-positive breast cancers and other cancers in humans.

Figure 1:
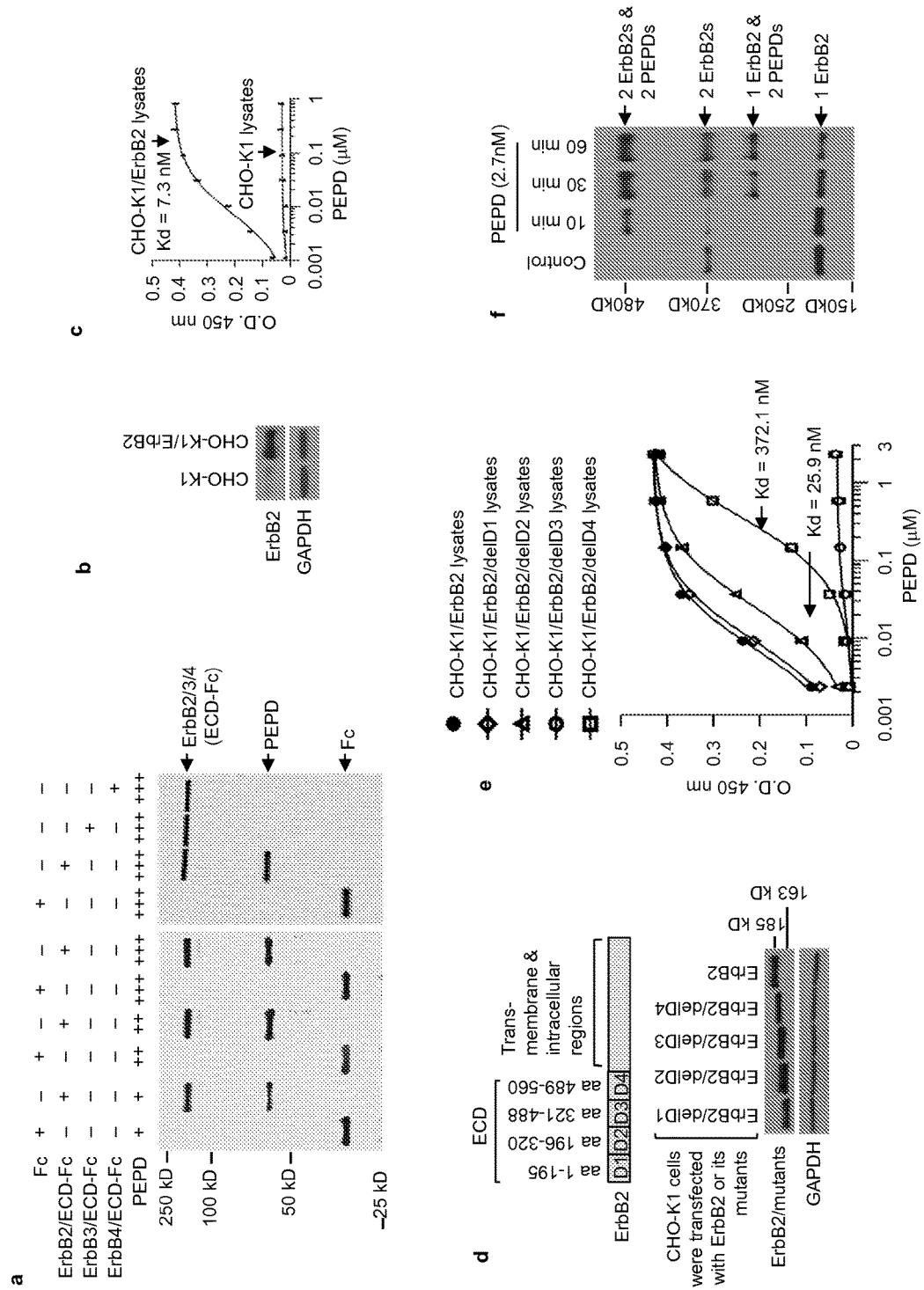
FIG. 1. Data demonstrating that PEPD binds to subdomain 3 of ErbB2 ECD and rapidly promotes ErbB2 dimerization. (a) PEPD at 0.04 µM (+), 0.2 µM (++) or 1 µM (+++) was incubated with ErbB2/ECD-Fc (0.04 µM), ErbB3/ECD-Fc (0.04 µM), ErbB4/ECD-Fc (0.04 µM) or Fc (0.04 µM), pulled down with protein G-sepharose, separated by SDS-PAGE, and stained with silver. (b) CHO-K1 cells were transfected with pCMV6-XL5-ERBB2 or the empty vector; 24 h later, cell lysates were prepared and analyzed by western blotting. Glyceraldehyde 3-phosphate dehydrogenase (GAPDH) was used here and elsewhere as a loading control. (c) PEPD binding to ErbB2, measured by ELISA (n=3), using cell lysates from b; same amount of lysates for all samples (25 µg protein per sample). Error bars indicate SD. (d) ErbB2 and its mutants; all gene transfections used the same amount of DNA and lasted for 24 h. Cell lysates were analyzed by western blotting. (e) PEPD binding to ErbB2 and its mutants, measured by ELISA (n=3), using cell lysates from d and an equal amount of ErbB2 or its mutants. Error bars indicate SD. (f) CHO-K1 cells stably overexpressing ErbB2 (CHO-K1/ErbB2 cells) were treated with PEPD. PEPD-treated cells and control cells were then treated with cross-linker bis(sulfosuccinimidyl)suberate (BS3) (2 mM, 30 min). Cell lysates were analyzed by western blotting using an ErbB2 antibody.
Figure 2:
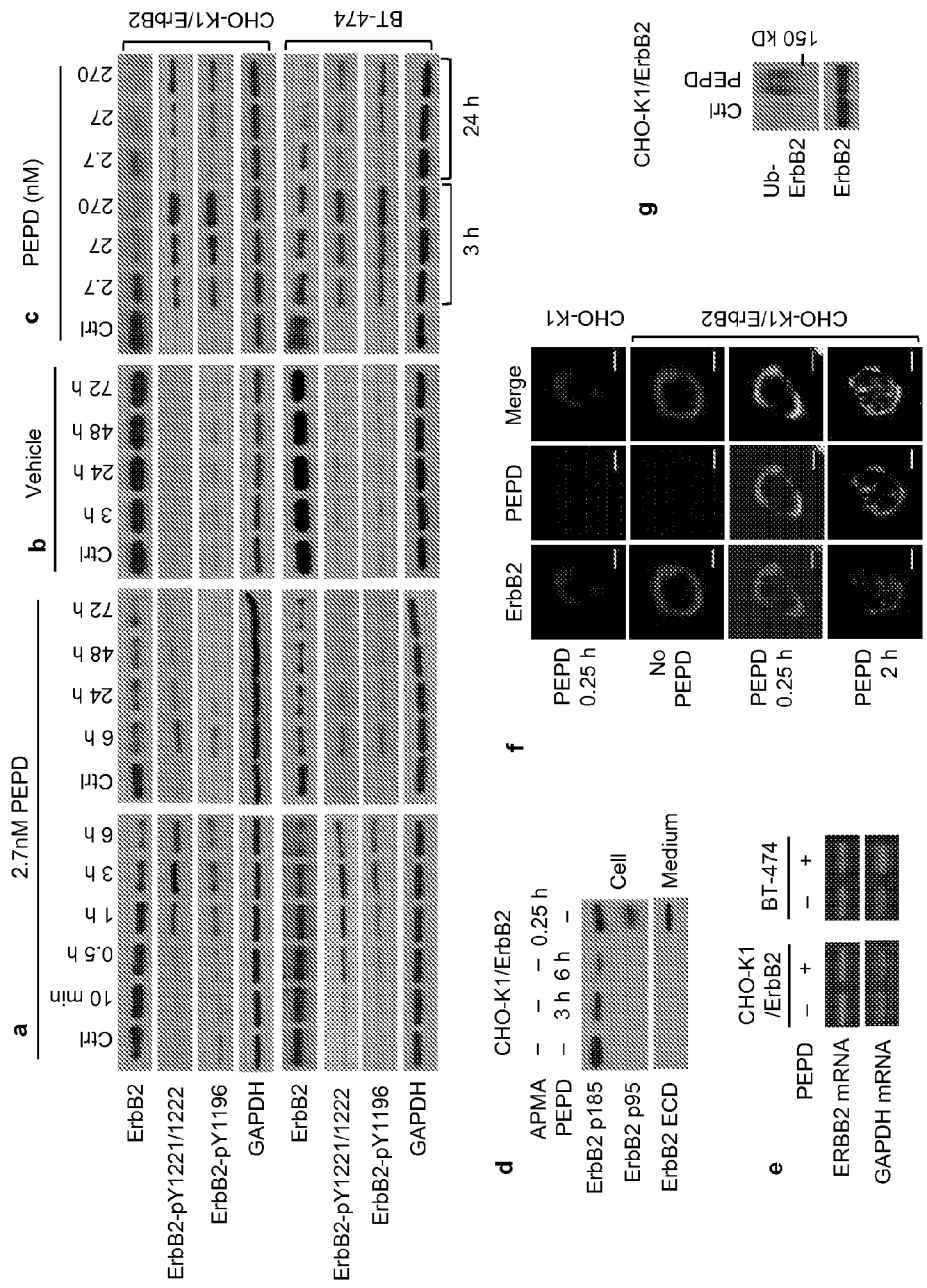
FIG. 2. Data showing ErbB2 Activation and depletion by PEPD. (a-c) Cells were treated with PEPD or vehicle; cell lysates were analyzed by western blotting. (d) Cells were treated with or without PEPD (270 nM), using 4-aminophenylmercuric acid (APMA) (1 mM) as a positive control. Cell lysates and media were analyzed by western blotting. (e) Cells were treated with or without PEPD (2.7 nM, 6 h), from which total RNA was isolated for RT-PCR. GAPDH was used as a control. (f) Cells were treated with or without PEPD (270 nM), followed by immunofluorescence staining of ErbB2 and PEPD and confocal microscopy. Scale bar: 10 μm. (g) Cells were transfected with ubiquitin (pMT107-His-Ub) and 24 h later treated with or without PEPD (2.7 nM, 0.5 h). Cell lysates were incubated with an ErbB2 antibody, pulled down with protein G-agarose, and analyzed by western blotting.
Figure 17:
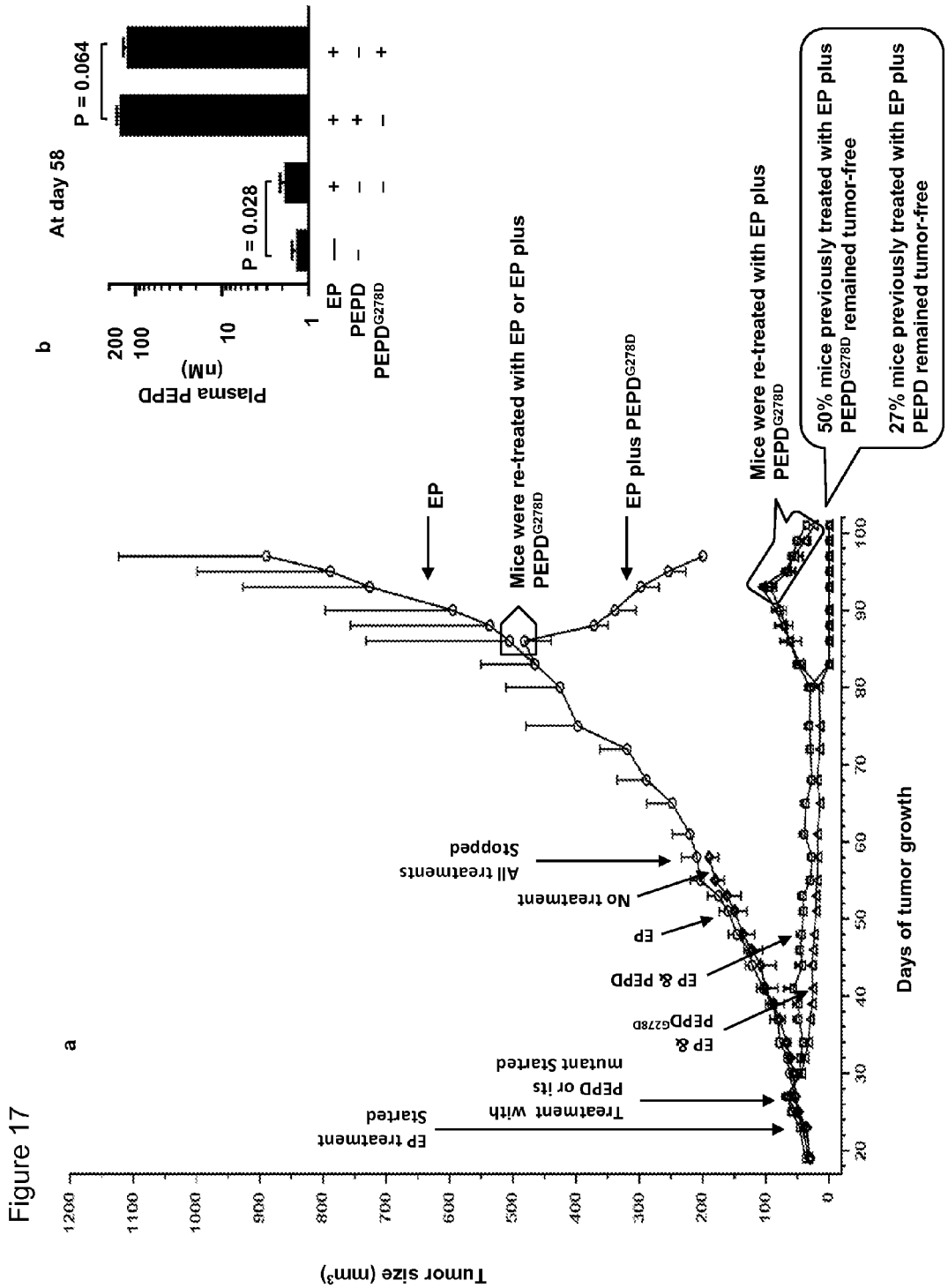
FIG. 17. Data showing strong inhibition of orthotopic mammary tumors by PEPD but stronger inhibition of the tumors by enzymatically inactive PEPD (PEPD$^{G278D}$). Female athymic nude mice (6-7 weeks of age) were each implanted subcutaneously (in the back) with a 60 day release of 17β-estradiol pellet (1.7 mg of estradiol), prior to orthotopic inoculation of breast cancer BT-474 cells into the mammary fat pads ($2 \times 10^6$ cells per site in a small volume of PBS:Matrigel mix). (a) Plot of tumor size over days of growth. EP (0.5 mg/kg) was given daily by intraperitoneal injection. Notably, EP at this dose was as effective as 2.5 mg/kg in elevating plasma level of PEPD. EP dosing was always started 4 days earlier than PEPD or PEPD$^{G278D}$. PEPD and PEPD$^{G278D}$ were given thrice weekly (Monday, Wednesday, Friday), each at 2 mg/kg by intraperitoneal injection. Each value is a mean±SEM. (b) Graph showing plasma PEPD in view of EP, PEPD and PEPD$^{G278D}$ treatments at day 58 of graph shown in panel a; each value is a mean±SD.
Figure 19:
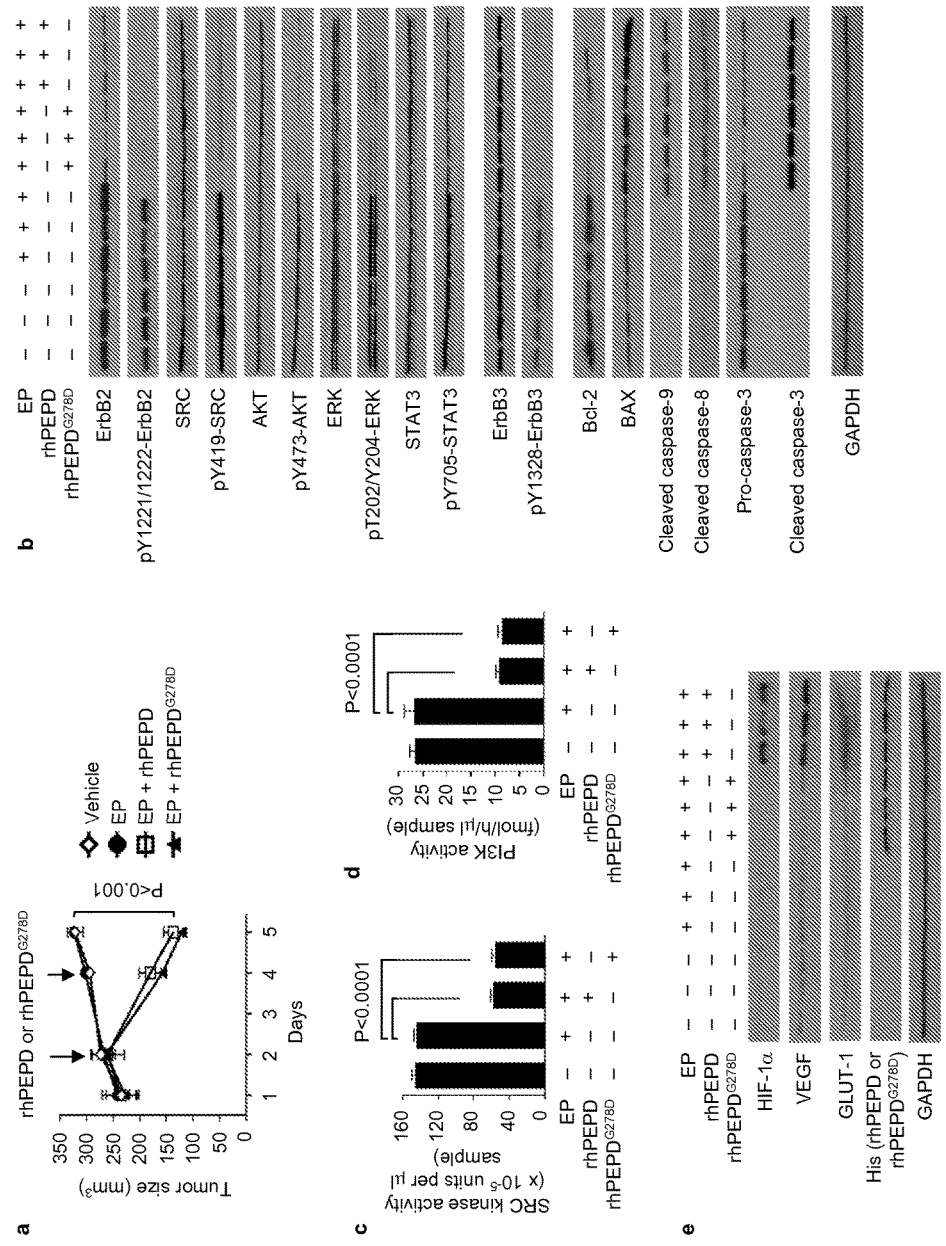
FIG. 19. Data summarizing tumor inhibition and molecular changes in tumors treated by rhPEPD or rhPEPD$^{G278D}$. rhPEPD or rhPEPD$^{G278D}$ are the same as PEPD or PEPD$^{G278D}$ or G278D-PEPD described before. Tumors in several experimental groups shown in FIG. 17 were too small for molecular analysis. (a) Sizes of tumors derived from mammary fat pad BT-474 cell xenografts upon treatment with vehicle, EP, EP plus rhPEPD or EP plus rhPEPDG278D. EP: daily at 0.5 mg per kg body weight intraperitoneally, started 4 days before rhPDPD or rhPEPD$^{G278D}$. rhPEPD or rhPEPD$^{G278D}$: 2 mg per kg body weight intraperitoneally, only two doses separated by 2 days. Error bars are s.e.m. (n=3-6). (b) Immunoblots comparing major cell signaling changes in tumor specimens obtained 24 h after the final dose as indicated in a. Each sample represents one tumor. (c, d) SRC kinase activity and PI3K activity in tumor specimens obtained 24 h after the final dose as indicated in a. Error bars are s.d. (n=3). (e) Immunoblots comparing HIF-1α signaling changes in tumor specimens obtained 24 h after the final dose as indicated in a. Each sample represents one tumor. As HIF-1α and related factors (vascular endothelial growth factor [VEGF] and glucose transporter 1 [GLUT-1]) are pro-survival factors, the result explains at least in part why rhPEPD$^{G278D}$ is a more powerful antitumor agent than rhPEPD is. The stimulatory effect of rhPEPD on these pro-survival factors is believed to depend on its dipeptidase activity. Both rhPEPD and rhPEPD$^{G278D}$ are internalized by tumor cells (measured by their His tag, FIG. 19e) apparently via ErbB2.

PEPD is a relatively high-affinity ligand (Kd=7.3 nM, FIG. 1c), and exerts potent impact on ErbB2 signaling. PEPD binds to subdomain 3 in the ErbB2 ECD, although the exact residues involved in binding remain undefined. While it was previously indicated that ErbB2 ECD adopts a fixed conformation that resembles a ligand-activated state, rendering it ready for homo- or hetero-dimerization in the absence of direct ligand binding (Cho H S, et a. Nature 2003, 421(6924): 756-760), the present disclosure indicate that this model is incomplete. PEPD causes a two-step ErbB2 signaling shutdown. Within minutes of PEPD treatment, the preassembled signaling complex of ErbB2-Src-CK2 is disrupted. Both Src and CK2 dissociate from ErbB2 and become inactivated, leading to changes in downstream signals: PTEN dephosphorylation and relocation to cell membrane, and AKT dephosphorylation (presumably due to PIP3 dephosphorylation by PTEN). However, PEPD has no effect on PI3K which apparently associates with ErbB2 via ErbB3. However, in vivo in the tumor tissues, PEPD as well as PEPD$^{G278D}$ silenced ErbB3 and PI3K (FIG. 19), apparently by disrupting ErbB2-ErbB3 association, which was not detected in our in vitro studies due to relatively short PEPD treatment times. Because the impact of PEPD on Src and CK2 occurs in the absence of apparent ErbB2 depletion, PEPD binding to ErbB2 dimer likely causes conformation change of the latter, rendering it unable to hold Src. PEPD also binds to ErbB2 monomer, causing ErbB2 dimerization and activation, which occurs somewhat slowly, as peak phosphorylation levels of ErbB2 and ERK were detected after 3 h of PEPD treatment. However, PEPD-induced ErbB2 activation is likely functionally insignificant, as PEPD also causes profound and sustained depletion of ErbB2, which became evident after 1-3 h of PEPD treatment and reached maximal depletion at 6 h, which was sustained for at least 72 h. PEPD was able to cause almost complete ErbB2 depletion (FIG. 2c). PEPD-induced ErbB2 depletion appears to result entirely from ErbB2 internalization and degradation, as PEPD has no effect on ErbB2 ECD cleavage, nor does it modulate ErbB2 gene expression. Thus, the present disclosure reveals a fundamentally different and new function of PEPD. PEPD has been known as a cytosolic dipeptidase. We have now learned that not only PEPD is an ErbB2 ligand, but a PEPD mutant which losses 99.4% of its dipeptidase activity is as effective as the wild type protein. Moreover, in vivo, the PEPD mutant is more efficacious than PEPD itself in combating ErbB2-driven tumors (FIG. 17). Intracellular PEPD has no effect on ErbB2, but PEPD is released from cells as revealed in the present disclosure, and more PEPD is released from damaged tissues and cells.

Compositions comprising PEPD are expected to be useful for prophylaxis and/or therapy of ErbB2-positive breast cancer and other cancers in humans. Consistent with its ability to rapidly silence the ErbB2-Src/CK2-PTEN-AKT signaling pathway, which plays a major role in ErbB2-driven breast cancer, and to cause pronounced and persistent depletion of ErbB2, we show that PEPD significantly inhibits the proliferation, anchorage-independent colony formation and invasion/migration of cells overexpressing ErbB2, while exerting little impact on cells that have minimum ErbB2 expression, and as described above and in more detail below, we demonstrate the anti-cancer effects of PEPD and an enzymatically inactive derivative thereof using clinically relevant animal models bearing Erb2+ tumors. The inhibitory impact of PEPD on ErbB2 stands in stark contrast to the well-known stimulatory impact of other ErbB ligands on their receptors. The impact of PEPD on ErbB2 signaling and cells overexpressing ErbB2 is reminiscent of that of trastuzumab. Given the high cost of trastuzumab use in the clinic (the current cost is >$1,000 per dose and about $70,000 for a full course of treatment), PEPD has the advantage that it can be mass produced as further described below at a relatively low cost, and is therefore expected in certain embodiments to be a significant and less expensive alternative to trastuzumab. In vivo, trastuzumab neither down regulates ErbB2 expression nor inhibits ErbB2 tyrosine phosphorylation in cancer tissues (Gennari et al., Clin Cancer Res, 10, 5650-5655, 2004; Gijsen et al., PLoS Biol, 8, e1000563, 2010); rather, its antitumor activity depends mainly on antibody-dependent cell-mediated cytoxicity (ADCC) via its Fc domain (Barok et al., Mol Cancer Ther, 6, 2065-2072, 2007; Clynes et al., Nature Med, 6, 443-446, 2000). Thus, PEPD or its mutant may complement trastuzumab and overcome to certain extent the resistance to trastuzumab in patients.

Any PEPD is expected to be suitable for use in the compositions and methods of the present disclosure. In embodiments, the PEPD is a PEPD produced by a prokaryote or a eukaryote. In embodiments, the PEPD is prokaryotic in origin. In non-limiting embodiments, the PEPD is produced by *Pseudoalteromonas haloplanktis* (i.e., a PEPD comprising the amino acid sequence under GenBank no. AAA99824.1), or *Pyrococcus furiosus* (i.e., a PEPD comprising the amino acid sequence under GenBank no. WP_011011876.1). A number eukaryotic PEPD amino acid sequences are also known in the art, including a number of mammalian PEPD amino acid sequences. In embodiments, the PEPD has the sequence of a rodent PEPD, i.e., a mouse or rat, or a non-human primate PEPD, such as chimpanzee or a Rhesus macaque. The amino acid sequence of mouse prolidase is provided under GenBank accession no. NP_032846.2; rat prolidase is provided under NP_001009641.1; Rhesus macaque prolidase is provided under AFJ71215.1; chimpanzee prolidase is provided under NP_001267459.1. The amino acid sequence of human prolidase (PEPD) in SEQ ID NO:1 is known in the art. SEQ ID NO:1 and the cDNA sequence encoding it is accessible via GenBank accession no. J04605.1; the amino acid sequence is also provided under GenBank accession number AAA60064. In one illustrative but not limiting embodiment, enzymatically active human PEPD has the sequence of SEQ ID NO:1:

```
                                         (SEQ ID NO: 1)
MAAATGPSFWLGNETLKVPLALFALNRQRLCERLRKNPAVQAGSIVVLQG

GEETQRYCTDTGVLFLQESFFHWAFGVTEPGCYGVIDVDTGKSTLFVPRL

PASHATWMGKIHSKEHFKEKYAVDDVQYVDEIASVLTSQKPSVLLTLRGV
```
-continued
```
NTDSGSVCREASFDGISKFEVNNTILHPEIVESRVFKTDMELEVLRYTNK

ISSEAHREVMKAVKVGMKEYGLESLFEHYCYSRGGMRHSSYTCICGSGEN

SAVLHYGHAGAPNDRTIQNGDMCLFDMGGEYYSVASDITCSFPRNGKFT

ADQKAVYEAVLLSSRAVMGAMKPGDWWPDIDRLADRIHLEELAHMGILSG

SVDAMVQAHLGAVFMPHGLGHFLGIDVHDVGGYPEGVERIDEPGLRSLRT

ARHLQPGMVLTVEPGIYFIDHLLDEALADPARASFLNREVLQRFRGFGGV

RIEEDVVVIDSGIELLTCVPRTVEEIEACMAGCDKAFTPFSGPK
```

In SEQ ID NO:1, the G at position 278 is shaded, bolded and italicized and represents the location of a G278D mutation which renders the PEPD enzymatically inactive. In embodiments, the mutation is a change of glycine at position 278 to an amino acid other than aspartic acid.

All of the amino acid and polynucleotide sequences provided under the GenBank accession numbers referenced in this disclosure are incorporated herein by reference as those sequences were available through GenBank on the date of filing of this application. This disclosure also includes all polynucleotides encoding PEPD and all variants of it that are described herein or which would otherwise be known to the skilled artisan given the benefit of the present disclosure.

Rodent (mouse and rat) PEPD amino acid sequences are more than 86% similar to the human sequence, while non-human primate PEPD amino acid sequences, such as the Rhesus macaque, is over 95% similar to the human PEPD amino acid sequence. In embodiments, the PEPD comprises or consists of a human PEPD amino acid sequence. In embodiments, the PEPD used in the compositions and/or methods of the present disclosure is at between at least 85.0% and 99.9%, inclusive, and including all numerals to the first decimal place there between, similar to the sequence of SEQ ID NO:1. In an embodiment, the PEPD comprises an amino acid sequence that is at least 95% similar to the sequence of SEQ ID NO:1.

In various embodiments, the present disclosure includes compositions comprising wild type PEPD (e.g., PEPD of SEQ ID NO:1), or modified PEPD, or a combination thereof. In general, modifications to PEPD suitable for use with the present invention can be determined by those skilled in the art using ordinary techniques, given the benefit of the present description. In embodiments, modified PEPD comprises modifications of SEQ ID NO:1. The disclosure includes all modifications of SEQ ID NO:1 so long as the PEPD retains the capability to bind to and cause depletion of ErbB2 from the cell surface. In embodiments, modified PEPD retains the capability to form a homodimer. In embodiments, contacting an ErbB2-positive cell with a modified (or wild type) PEPD of this disclosure is followed by ErbB2 binding and endocytosis of ErbB2, resulting in ErbB2 depletion. Modified PEPD that maintain some or all of these functional attributes may comprise amino acid insertions, deletions and substitutions. For example, the disclosure includes PEPD which has been modified by conservative amino acid substitutions that are based generally on relative similarity of R-group substituents. Non-limiting examples of such substitutions include gly or ser for ala; lys for arg; gln or his for asn; glu for asp; ser for cys; asn for gln; asp for glu; ala for gly; asn or gln for his; leu or val for ile; ile or val for leu; arg for lys; leu or tyr for met; thr for ser; tyr for trp; phe for tyr; and ile or leu for val. Thus, a PEPD that comprises any single conservative amino acid substitution, or any combination of conservative amino acid substitutions, are included in the disclosure provided they can at least retain the capability to bind to ErbB2, with subsequent depletion of ErbB2 from the cell surface. It will be apparent to those skilled in the art how to determine whether or not any particular modified PEPD can bind to ErbB2. In embodiments, the modified PEPD can bind the ErbB2 extracellular domain with an estimated Kd value of 7.3 nM, as determined using an ELISA assay.

Wild type PEPD is enzymatically active. Modified PEPD is a PEPD that comprises a change in SEQ ID NO:1 and can be enzymatically active or enzymatically inactive. In this regards, it is known in the art that defects in the iminodipeptidase activity of PEPD is associated with Polidase Deficiency, which is a very rare autosomal recessive disease associated with collagen metabolism and affects connective tissues. Thus it is known that the enzymatic activity of PEPD is important. However, in embodiments, enzymatically inactive PEPD is used in the compositions and methods of this disclosure. Enzymatically inactive PEPD is considered to be a PEPD that exhibits less hydrolysis of a substrate dipeptide that has proline or hydroxyproline at its carboxy terminus than the amount of such hydrolysis exhibited by a reference protein which comprises or consists of the sequence of SEQ ID NO:1. In embodiments, enzymatically inactive PEPD can have at least between 0.0%-99.9%, inclusive, and including all digits there between to the first decimal point, less dipeptide hydrolysis activity as compared to a reference PEPD. In one embodiment, an enzymatically inactive PEPD has no more than 0.6% dipeptide hydrolysis activity of a reference PEPD. In one embodiment, the reference PEPD comprises or consists of the sequence of SEQ ID NO:1. One unit of prolidase activity can be defined as the amount of enzyme that releases 1 μmol of proline/h under standard assay conditions. In one embodiment, an enzymatically inactive PEPD has no detectable PEPD dipeptide hydrolysis activity. In an embodiment, an enzymatically inactive PEPD comprises a G278D mutation. In embodiments, the disclosure includes any one, or any combination of PEPD mutations disclosed herein, and accordingly includes the proviso that any single or any combination of such mutants can be excluded from the invention.

PEPD used in embodiments of this disclosure can include modifications that enhance its desirable characteristics, such as the capability to bind to or enter a tumor cell or tumor microenvironment, or to enhance circulation time, bioavailability, stability, or uses related to ErbB2-positive cell-targeted killing, or ErbB2-positive cell imaging. PEPD proteins that can be used with the present disclosure include a polypeptide comprising SEQ ID NO:1 or a modification thereof, and in embodiments also include such PEPD polypeptides within the context of a larger polypeptide. Modifications to SEQ ID NO:1 include modifications that abrogate or lessen enzymatic activity, and/or changes that do not affect the capability of the modified PEPD to bind to ErbB2. Thus, the PEPD of SEQ ID NO:1 can be modified by conservative amino acid substitutions that are based generally on relative similarity of R-group substituents. Non-limiting examples of such substitutions contemplated include, but are not limited to: gly or ser for ala; lys for arg; gln or his for asn; glu for asp; ser for cys; asn for gln; asp for glu; ala for gly; asn or gln for his; leu or val for ile; ile or val for leu; arg for lys; leu or tyr for met; thr for ser; tyr for trp; phe for tyr; and ile or leu for val. Thus, PEPDs that comprise any single conservative amino acid substitution, or any combination of conservative amino acid substitutions, are included in this disclosure, so long as they retain their ErbB2-binding properties, and can inhibit growth of ErbB2-positive cells. Thus, the instant disclosure includes polypeptide sequences that comprise SEQ ID NO:1 or modifications thereof, and can include further modifications, including but not necessarily limited to additional amino acids, and/or by being provided as part a complex with other compositions of matter. Thus, the PEPD polypeptides could be part of larger proteins, such as fusion proteins, or they could be connected to other moieties. Accordingly, the PEPD proteins could be covalently or non-covalently associated with any desirable moiety that would be expected to improve their functional capabilities in accordance with the prophylaxis and/or therapy of ErbB2-positive cancers.

In general, the PEPD protein (and if desired a polypeptide sequence with which it is made as a single fusion protein) can be made using conventional techniques. For example, in embodiments, PEPD protein/fusion protein can be made using prokaryotic or eukaryotic expression systems. Thus, the disclosure provides manufacturing advantages over other ErbB2 binding partners, such as mAbs directed at ErbB2, which are expensive and time consuming to make. For recombinant production of proteins comprising or consisting of a PEPD as described herein, in general, any polynucleotide encoding the PEPD can be provided in an expression vector. "Expression vector" refers to a vector comprising protein expression control sequences operatively linked to the PEPD coding sequence. The expression vector can comprise cis-acting elements for expression, including but not limited to promoter elements, enhancer elements, origins of replication, selectable markers, transcription initiation sites, sequences that encode translation initiation sites, and any other sequence that is desirable for protein expression, depending on the expression system chosen. Suitable protein expression vectors which can be designed to express any polynucleotide sequence encoding PEPD (each of which PEPD-encoding sequences is encompassed within this disclosure) include all those known in the art, examples of which include but are not limited to cosmids, plasmids and virus-based systems that incorporate the recombinant polynucleotide encoding the PEPD. The system used to express the recombinant PEPD proteins of the invention can be any suitable organism and include but are not limited to mammalian cell expression systems, insect cell expression systems (e.g., baculovirus-based systems), yeast expression systems, plant cell expression systems, and prokaryotic expression systems. In one embodiment, $E.\ coli$ is used for PEPD expression. In one embodiment, a PEPD chimeric protein is expressed recombinantly using a mammalian expression system so that the chimeric protein comprises human-specific glycosylation.

In an embodiment, a PEPD protein can be conjugated to an immunoglobulin (Ig) or a fragment thereof to provide a chimeric PEPD/Ig molecule. Such a construct is expected to be useful in involving various aspects of the immune response of the individual to facilitate targeted killing of ErbB2+ cells. The immunoglobulin or fragment thereof can be any Ig type or subtype. In this regard, previous studies have indicated that antibody-dependent cellular cytotoxicity (mediated via Fc receptors) plays a critical part in trastuzumab targeting of ErbB2-positive breast cancer (Clynes et al., Nature Med, 6, 443-446, 2000; Spiridon et al., Clin Cancer Res, 10, 3542-3551, 2004). The present disclosure likewise encompasses PEPD-Fc chimeric proteins and pharmaceutical compositions comprising them. Methods for making Fc-chimeric proteins are known in the art. For example, pFUSE-Fc vectors, commercially available from InvivoGene, can be used to generate PEPD-Fc fusion hybrids. Thus, in one embodiments the disclosure includes a composition comprising a fusion protein, wherein the PEPD in a component of the fusion protein, and wherein the fusion protein comprises an Fc region of a human Ig. In various embodiments, the Fc region is an Fc region or fragments thereof is from an IgA, IgG, or IgE antibody, although Fc regions from other antibody types, or synthetic/artificial Fc regions can also be used. In embodiments, the Fc region is a human IgG2a or human IgG1 or a fragment of such Fc regions. The Fc region can comprise or consist of an amino acid sequence that is identical to an Fc region produced by a mammal, such as a human. In various embodiments, the Fc region may have between 80% to 100% (including all integers there between) amino acid sequence similarity to an Fc region produced by a mouse and/or a human. The Fc region may be an intact Fc region, meaning an entire Fc region, or may be a fragment of the Fc region. Those skilled in the art will recognize that the "Fc region" of an antibody means the "Fragment, crystallizable" region of the antibody, which comprises two heavy chains that contribute two or three constant domains (CD) depending on the class of the antibody. Nucleotide sequences encoding Fc regions, as well as the amino acid sequences of Fc regions for mouse and human immunoglobulins are well known in the art. In one embodiment, the Fc portion of the fusion proteins comprises only antibody heavy chain(s). Those skilled in the art will recognize that for demonstration of the invention using murine animal models, the Fc portion of the fusion protein may be an IgG2a or IgG2b Fc murine Ig portion, while for therapy and/or prophylaxis of disease in humans, the Fc portion is preferably an IgG1 or an IgG3 Fc portion. In certain embodiments, the Fc portion of the fusion proteins provided herein do not include antigen recognition portions (i.e., the antibody portion of the fusion proteins do not contain antibody variable regions). Thus, the fusion proteins are distinct from antibodies that do contain antigen binding portions. DNA constructs encoding the Fc-fusion PEPD proteins can be made using any conventional techniques well known to those skilled in the art. For example, the Fc-fusion encoding constructs can be made using commercially available reagents. For instance, INVIVOGEN offers the pFUSE-Fc family of plasmids developed to facilitate the construction of Fc-Fusion proteins by fusing a sequence encoding a given protein to the Fc region of an immunoglobulin (Ig). In this construct, the Fc region comprises the CH2 and CH3 domains of the IgG heavy chain and the hinge region. The hinge acts as a flexible spacer between the two parts of the Fc-fusion protein, which permits each part of the fusion protein to function independently if desired.

As described above, the disclosure includes any PEPD protein as a component of a fusion protein which can include any other amino acid sequence that would be desirable for expressing in the same open reading frame as the PEPD protein, and can include but are not limited to amino acid sequences involved in facilitating protein isolation and/or purification, for solubility, secretion, or any other function. The PEPD polypeptide can be configured N-terminal or C-terminal to the fused open reading frame, depending on the particular fusion protein to be produced. For example, the PEPD proteins can be provided with a histidine tag, such as a suitable polyhistidine tag. In embodiments, the histidine tag comprises at least six histidines in sequence. In an embodiment, the his tag is a hexa-histidine peptide sequence. In an embodiment, if desired, a PEPD expression system can be configured so that the histidine tag can be removed, such as by including a tobacco etch virus (TEV)-cleavable, N-terminal hexa-histidine tag.

In non-limiting embodiments, the PEPD polypeptides can be combined with or coupled to a chemotherapeutic agent, or any other agent that has cytotoxic activity, or agents that are useful for detection and/or imaging of ErbB2-positive cells/tissues. For example, PEPD conjugates may include enzymatically active toxins and fragments thereof or small molecules. Suitable enzymatically active toxins and small molecules include but not limited to docetaxel, mitoxanthrone, taxanes, diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes, microtubule-targeting agents, or any anti-angiogenic agent(s).

Conjugates and combinations of the PEPD protein and chemotherapeutic agents (or other agents, such as imaging agents) may be made using any suitable techniques. In various embodiments, the PEPD protein can be produced separately from the chemotherapeutic agent, and then chemically coupled to it, or in the case of protein agents, the PEPD protein can be produced as a PEPD/protein fusion to yield a novel chimeric protein. For chemical coupling, a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene) can be used to covalently join a PEPD and a chemotherapeutic or other agent, such as an imaging agent.

In another embodiment, the PEPD can be conjugated to a radioactive agent. A variety of radioactive isotopes are available for conjugating to proteins such that ErbB2-positive cells or tissues to which the PEPD bind can be imaged or selectively destroyed. For selective destruction of cells the peptides can be conjugated to a highly radioactive atom, such as At211, I131, I125, Y90, Re186, Re188, Sm153, Bi212, P32, Pb212 and radioactive isotopes of Lu. For identifying ErbB2-positive cells, the PEPD conjugates can include a radioactive atom for scintigraphic studies, for example Tc99m (metastable technetium-99), I123, or a spin label for nuclear magnetic resonance and/or magnetic resonance imaging, such as I123, I131, In111, F19, C13, N15, O17 or Gadlinium (III) or Manganese (II). The radio-labels may be incorporated in the PEPD proteins in known ways.

The PEPD proteins can be provided in pharmaceutical compositions for administration by combining them with any suitable pharmaceutically acceptable carriers, excipients and/or stabilizers. Some suitable examples of pharmaceutically acceptable carriers, excipients and stabilizer can be found in *Remington: The Science and Practice of Pharmacy* (2005) 21st Edition, Philadelphia, Pa. Lippincott Williams & Wilkins. Further, any suitable delivery vehicle can be used in the invention, such as a controlled release delivery formulation in which the PEPD is released over a period of time. If desired, the pharmaceutical composition can comprise both PEPD and a coagulation inhibitor.

Administration of formulations comprising PEPD as described herein can be performed using any suitable route of administration, including but not limited to parenteral, intraperitoneal, intrapulmonary, oral, and intra-tumoral. Parenteral infusions include intramuscular, intravenous, intraarterial, intraperitoneal, and subcutaneous administration.

The amount PEPD and any other active agent to be included in a composition and/or to be used in the method can be determined by those skilled in the art, given the benefit of the present disclosure. Thus, in one embodiment, an effective amount of a composition of the invention is administered. An effective amount can be an amount of the composition that inhibits growth of cells in the individual that express ErbB2, or an amount that extends the survival of the individual, or that alleviates disease symptoms associated with expression of the ErbB2 in the individual, or suppresses a malignant phenotype of cells overexpressing ErbB2. In embodiments, the individual to whom a composition of the invention is administered has, is suspected of having, or is at risk for development and/or recurrence of an ErbB2-positive cancer. In embodiments, the ErbB2-positive cancer is a breast cancer, bladder cancer, ovarian cancer, stomach cancer, or aggressive forms of uterine cancer, such as uterine serous endometrial carcinoma, or other cancers overexpressing ErbB2, or cancers whose stem cells overexpress ErbB2, or metastatic cancers overexpressing ErbB2.

Suitable dosages for either therapeutic or prophylactic purposes can be determined by those skilled in the art and will be based, at least in part, on consideration of the individual's age, sex, size, and health, the type of delivery system used, the stage of disease, and other factors as will be apparent to the skilled artisan. In embodiments, PEPD dosing for human subjects may be similar to or the same as dosing for trastuzumab, which is typically 2-4 mg/kg weekly.

Compositions of the disclosure can be administered in conjunction with any conventional treatment regimen, including sequential or simultaneous administration of chemotherapeutic agents, passive immunotherapies, vaccines, adjuvants, the like. In particular embodiments, the method can be performed in conjunction with conventional therapies that are intended to treat a disease or disorder associated with ErbB2-positive cells. For example, administration of compositions described herein can be combined with treatment modalities including but not limited to chemotherapies, surgical interventions, and radiation therapy which can be performed prior to, concurrently, or subsequent to PEPD administrations. In embodiments, the disclosure includes a composition comprising PEPD and cetuximab, a clinically used monoclonal antibody against ErbB1. In embodiments, the disclosure includes a composition comprising PEPD with the clinically used dual ErbB1/ErbB2 kinase inhibitor lapatinib. In embodiments, the disclosure includes compositions comprising PEPD and trastuzumab. In embodiments, the disclosure includes compositions comprising PEPD and pertuzumab, another clinically used anti-ErbB2 monoclonal antibody.

In embodiments, the disclosure includes compositions and methods for using the compositions, wherein in addition to a PEPD protein, the compositions comprise a blood coagulation inhibitor. In one embodiment, the coagulation inhibitor is an agent that inhibits PEPDs degradation in vivo, so as to reduce PEPD dose required by patients. In one embodiment, the coagulation inhibitor inhibits conversion of prothrombin to thrombin, or inhibits the participation of thrombin in clot formation. In an embodiment, the coagulation inhibitor interferes with the clotting related function of the clot-promoting proteins known as factor X and factor II. In embodiments, the coagulation inhibitor binds to and activates antithrombin III, and as a consequence, coagulation factors Xa and IIa are inhibited. In an embodiment, the coagulation inhibitor is heparin, such as an unfractionated heparin preparation, or a low molecular weight form of heparin. Low molecular weight forms of heparin are known in the art (i.e., Weitz J I; Weitz, Jeffrey I. (1997). "Low-molecular-weight heparins". N Engl J Med 337 (10): 688-98). In an embodiment, the low molecular weight heparin is enoxaparin or a pharmaceutically acceptable salt thereof, such as enoxaparin sodium. In an embodiment, the inhibitor is a direct Xa inhibitor, either oral or non-oral, including but not limited to the drugs sold under the trade names RIVAROXABAN, APIXABAN or EDOXABAN. In an embodiment, the coagulation inhibitor may be an inhibitor of other blood coagulation factors, including but not limited to Factors XII, XI and VII. In embodiments, the low molecular weight heparin or other coagulation inhibitor is administered using any suitable vehicle and route of administration. In embodiments, the coagulation inhibitor is administered by subcutaneous injection. In one embodiment, the coagulation inhibitor is administered orally. The dose of the coagulation inhibitor can be based on the individual recipient's weight and other parameters that will be recognized by those skilled in the art given the benefit of this disclosure. In embodiments, the coagulation inhibitor can be given prior to, concurrent with, or subsequent to the PEPD composition, and may be administered with the same number and timing of the PEPD administration(s), or may be administered according to a schedule that is different than the PEPD administration.

In another embodiment, the present disclosure provides a method for identifying whether an individual is a candidate for treatment with a composition comprising a PEPD. The method comprises obtaining a biological sample from the individual and determining whether the sample comprises ErbB2-positive cancer cells, wherein determining that the biological sample comprises ErbB2-positive cancer cells is indicative that the individual is a candidate for the treatment, and wherein determining that the biological sample does not comprise ErbB2-positive cancer cells is indicative that the individual is not a candidate for the treatment. Thus, in embodiments, the present disclosure provides for aiding in the diagnosis, or for diagnosing an individual as in need of treatment with a composition comprising a PEPD. In embodiments, the method comprises communicating a determination of presence or absence of ErbB2-positive cancer cells in the biological sample to a health care provider so that the health care provider can, in one embodiment, recommend treatment with a composition comprising a PEPD. In embodiments, the method further comprises administering a composition comprising a PEPD to the individual. A determination of the presence of ErbB2-positive cancer cells comprises detecting in an individual or a biological sample obtained from the individual's cancer cells which overexpress ErbB2.

In an embodiment, the method of identifying whether an individual is a candidate for treatment with a composition comprising a PEPD comprises obtaining a biological sample from the individual and determining whether the sample comprises ErbB2-positive cancer cells and/or overexpresses ErbB2 by contacting the sample with a detectably labeled PEPD. Detecting a complex of ErbB2+ and detectably labeled PEPD is indicative that the individual is a candidate for treatment with a composition comprising PEPD as described herein. In an embodiment, the complex of ErbB2+ and detectably labeled PEPD is detected on a biopsy of a tumor that is suspected of comprising ErbB2-positive cells. In alternative embodiments, PEPD bound to an ErbB2-positive cell can be detected by using a detectably labeled PEPD binding partner. In embodiments, ErbB2-positive cancer cells express more ErbB2 than a reference. The reference can be any suitable reference, such as a matched control, a standardized value (i.e., area under a curve), and/or values for ErbB2 amounts expressed by a cell of the same tissue type in a sample, wherein the ErbB2 cells are not cancer cells. In general, in certain embodiments, identification of a human subject as a candidate for treatment with a PEPD formulation is performed using the same or similar criteria as for identifying an individual as a candidate for therapy with trastuzumab, which is based on clinically established parameters and will be known to the skilled artisan. For example, immunohistochemistry (IHC) is frequently used to measure the amount of ErbB2 present in a tumor biopsy sample, or alternatively fluorescence in situ hybridization (FISH) is used to measure the number of copies of the gene (see, for example, Carlson R W et al., J Natl Compr Canc Netw 2006, Suppl 4, S1-22; Her2 testing in breast cancer: NCCN Task Force report and recommendations.). In embodiments, a tumor with an IHC score of 0 or 1+, an average ErbB2 gene/chromosome 17 ratio of less than 1.8, or an average number of ErbB2 gene copies/cell of 4 or less as determined by FISH is considered to be ErbB2 negative. A tumor sample with an IHC score of 3+, an average ErbB2 gene/chromosome 17 ratio of greater than 2.2 by FISH, or an average number of ErbB2 gene copies/cell of 6 or greater is considered ErbB2 positive within the context of identifying individuals who are candidates for cancer therapy using agents that target ErbB2.

In embodiments the disclosure further provides products, e.g. articles of manufacture, which comprise PEPD pharmaceutical preparations. The products comprise isolated and/or purified PEPD. The PEPD can be an enzymatically active or inactive form of PEPD. The articles of manufacture include packaging and/or printed material. In one embodiment, the instant disclosure includes a closed or sealed package that contains a PEPD preparation. In certain embodiments, the package can comprise one or more closed or sealed vials, bottles, blister (bubble) packs, or any other suitable packaging for the sale, or distribution, or use of the PEPD pharmaceutical agents. The printed material can include printed information. The printed information can be provided on a label, or on a paper insert, or printed on the packaging material itself. The printed information can include information that identifies the PEPD agent in the package, the amounts and types of other active and/or inactive ingredients, and instructions for taking the composition, such as the number of doses to take over a given period of time, and/or information directed to a pharmacist and/or another health care provider, such as a physician, or a patient. The kit can comprise and the printed information can identify an additional agent, such as a coagulation inhibitor, that is provided separately or in combination with the PEPD agent. The printed material can include an indication that the PEPD pharmaceutical composition and/or any other agent provided with the kit is for the treatment of an ErbB2-positive cancer. The product can be provided as a kit comprising a therapeutically effective amount of a PEPD composition, packaged in a container, the kit further comprising a label attached to or packaged with the container, the label describing the contents of the container and providing indications and/or instructions regarding use of the contents of the container to treat ErbB2-positive cancer.

The following Examples are intended to illustrate but not limit the invention.

Example 1

This Example demonstrates that human PEPD binds to subdomain 3 in the human ErbB2 ECD and causes ErbB2 dimerization.

Figure 7:
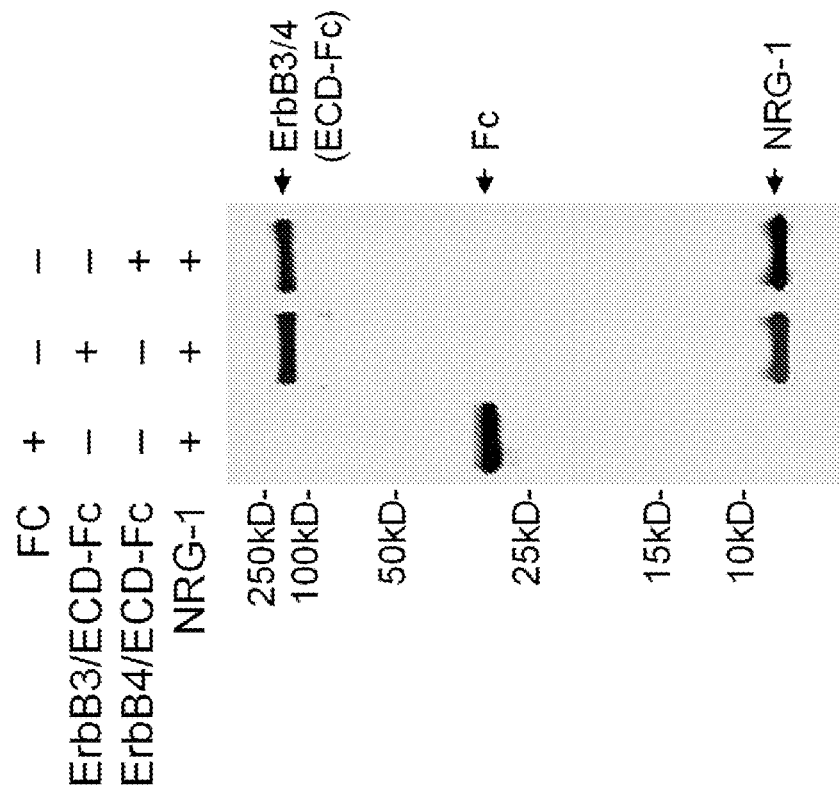
FIG. 7. Data showing binding of neuregulin-1 (NRG-1) to the ECDs of ErbB3 and ErbB4. NRG-1 at 0.2 μM was incubated with Fc (0.04 μM), ErbB3/ECD-Fc (0.04 μM) or ErbB4/ECD-Fc (0.04 μM), pulled down with protein G-sepharose, separated by SDS-PAGE (15%), and stained with silver. This demonstrates that both ErbB3/ECD-Fc and ErbB4/ECD-Fc were biologically functional with regarding to the results shown in FIG. 1.
Figure 8:
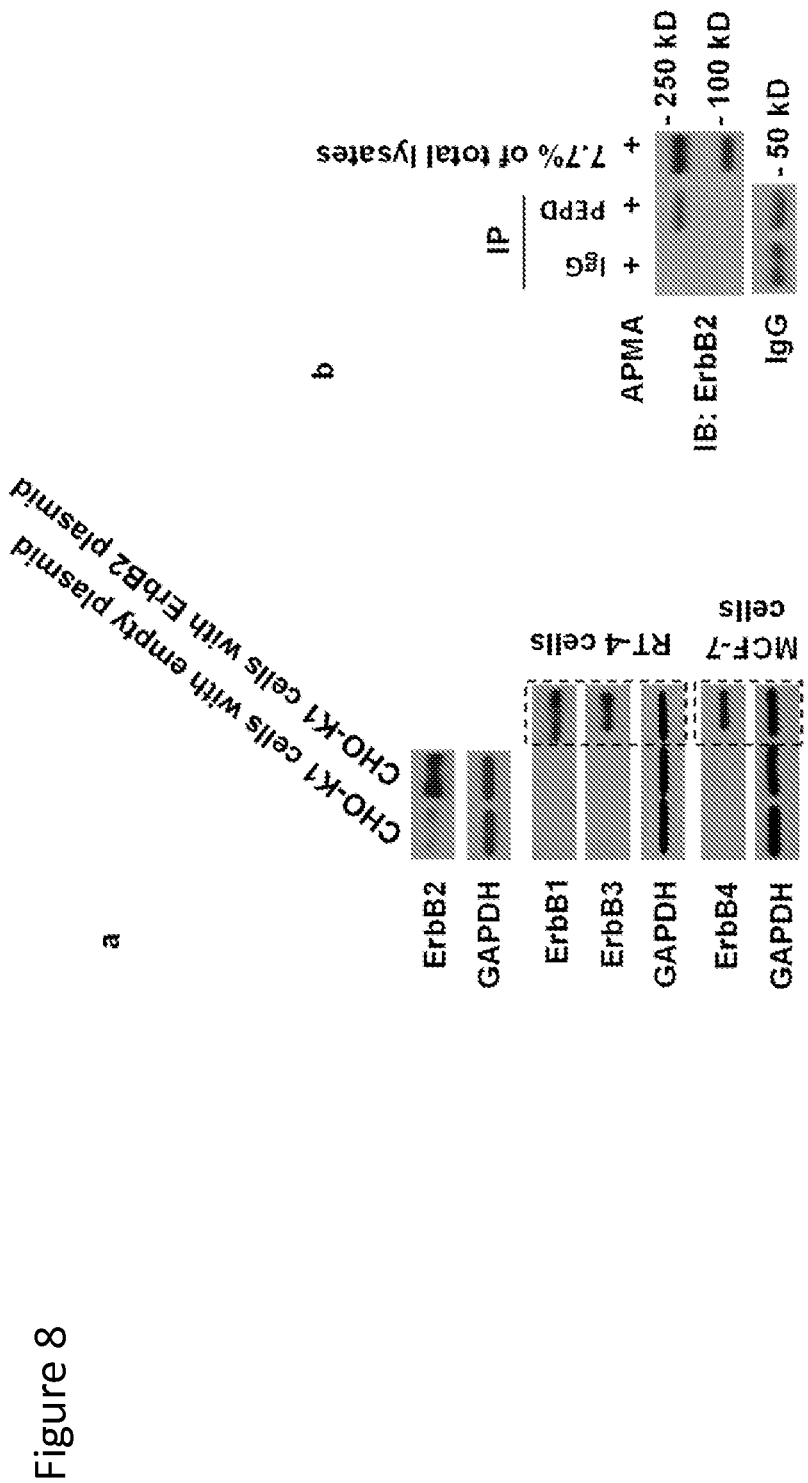
FIG. 8. Data showing validation of a cell line used in the present disclosure, and lack of binding of PEPD to the transmembrane and intracellular regions of human ErbB2. (a) CHO-K1 cells were transiently transfected with an ErbB2-expressing plasmid (pCMV6-XL5-ERBB2) or the empty plasmid for 24 h. Human bladder cancer RT-4 cells and human breast cancer MCF-7 cells were untreated and were used as positive controls for ErbB1, ErbB3 and ErbB4. Cell lysates were analyzed by western blotting. GAPDH is a loading control. (b) CHO-K1 cells stably expressing ErbB2 (CHO-K1/ErbB2 cells) were treated with 1 mM APMA for 0.25 h. Cell lysates were then prepared and analyzed by western blotting (the first lane on the right). The same cell lysates were mixed with 1 μM PEPD, which were then incubated with a PEPD antibody or an isotype-matched IgG, pulled down with protein G-agarose, and analyzed by western blotting. The result shows that APMA causes ErbB2 ECD cleavage, as expected, generating the p95 fragment (minus ECD), but PEPD only co-precipitates with the intact ErbB2, not the p95 fragment, indicating that PEPD does not bind to the trans-membrane or intracellular regions of ErbB2.

Recombinant human PEPD was generated in bacteria as described further below and was incubated at 0.04, 0.2 or 1 μM with 0.04 μM of ErbB2/ECD-Fc [a recombinant chimera of human ErbB2 ECD (Thr23-Thr652) and the Fc fragment of human IgG$_1$] or 0.04 μM of Fc as a control. PEPD bound specifically to the ECD, and each PEPD subunit bound maximally to one copy of ECD (FIG. 1a). Given that both PEPD and ErbB2/ECD-Fc (due to Fc) form homodimers in solution, the above result indicates that one PEPD dimer binds to one ECD dimer. PEPD was also incubated at 1 μM with 0.04 μM of ErbB3/ECD-Fc [a chimera of the ECD (Ser20-Thr643) of human ErbB3 and Fc] or 0.04 μM of ErbB4/ECD-Fc [a chimera of the ECD (Gln26-Arg649) of human ErbB4 and the Fc], but no binding could be detected (FIG. 1a). As expected, neuregulin-1 (NRG-1) bound to the ECDs of ErbB3 and ErbB4 (FIG. 7). Thus, PEPD is not a ligand of ErbB3 or ErbB4. We further studied PEPD binding to ErbB2 using Chinese hamster ovary CHO-K1 cells, which expressed a low level of ErbB2 but none of the other ErbBs (FIG. 8a). Overexpression of human ErbB2 in CHO-K1 cells was readily achieved by gene transfection (FIG. 1b). In an enzyme-linked immunosorbent assay (ELISA) using the lysates of ErbB2-overexpressing cells, PEPD bound to ErbB2 with an estimated Kd value of 7.3 nM, whereas there was little PEPD binding to the lysates of control CHO-K1 cells (FIG. 1c). PEPD did not bind to the trans-membrane and intracellular regions of ErbB2 (FIG. 8b). Next, we removed the four ECD subdomains of human ErbB2 one at a time (FIG. 1d), using the ErbB2-expressing plasmid pCMV6-XL5-ERBB2 as a template. Similar protein expression levels of ErbB2 and its mutants were detected in CHO-K1 cells transiently transfected with the plasmids (FIG. 1d). An equal amount of ErbB2 and its mutants, based on western blot quantification, were used in the same ELISA mentioned above. Subdomain D1 deletion had little impact on PEPD-ErbB2 binding; the binding affinity after removing subdomains D2 and D4 was reduced 3.5 fold and 51.0 fold, respectively, but full PEPD binding was achieved by raising the PEPD concentration; removing subdomain D3 completely abolished PEPD binding (FIG. 1e). Thus, PEPD bound to D3, but D2 and D4, the latter in particular, may facilitate PEPD binding to ErbB2.

Overexpression of ErbB2 in cell is known to cause spontaneous dimerization. As expected, both monomers and dimers of ErbB2 existed in CHO-K1 cells stably overexpressing ErbB2 (FIG. 1f). Cells were treated with crosslinker bis(sulfosuccinimidyl)suberate (BS3) before harvest and western blot analysis. PEPD apparently underwent two phases of ErbB2 binding: rapid binding of PEPD homodimers to preexisting ErbB2 homodimers (no change in ErbB2 monomer level, decrease in ErbB2 dimer level and formation of heterotetramer of 2 ErbB2s and 2 PEPDs at 10 min of PEPD treatment), followed by binding of PEPD homodimer to ErbB2 monomer, which was apparent at 30 min of PEPD treatment (decrease in ErbB2 monomer level, formation of heterotrimer of 1 ErbB2 and 2 PEPDs, formation of new ErbB2 homodimer, and further increase in heterotetramer of 2 ErbB2s and 2 PEPDs) (FIG. 1f). Notably, presence of ErbB2 homodimers not linked to PEPD after PEPD treatment likely resulted from incomplete cross-linking of the two proteins by BS3.

Example 2

Figure 9:
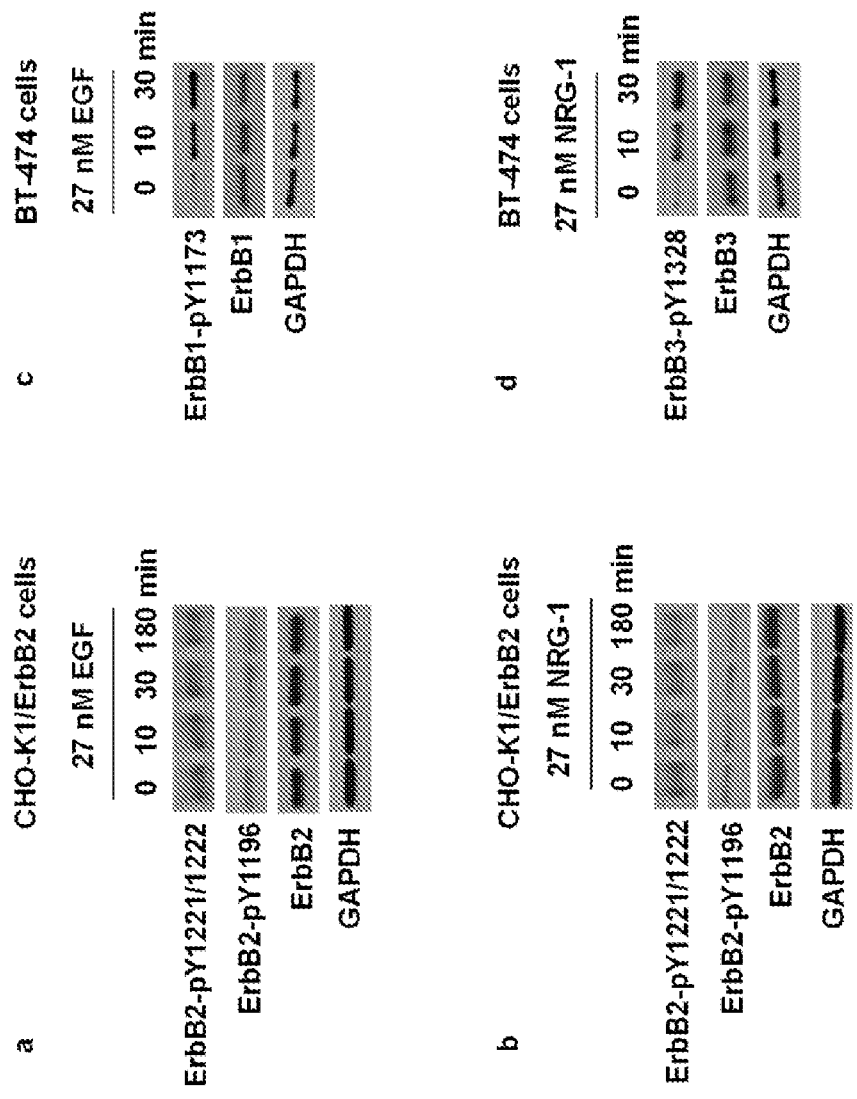
FIG. 9. No effects of epidermal growth factor (EGF) and NRG-1 on ErbB2. (a, b) CHO-K1 cells stably overexpressing human ErbB2 (CHO-K1/ErbB2 cells) were treated with recombinant EGF or recombinant NRG-1. Cells lysates were then prepared and analyzed by western blotting. (c, d) In order to ensure that both EGF (ligand of ErbB1) and NRG-1 (ligand of ErbB3 and ErbB4) that were used in our experiments were bioactive, they were evaluated in BT-474 cells, which expressed relatively low levels of ErbB1 and ErbB3. As expected, EGF significantly stimulated ErbB1 phosphorylation, and NRG-1 significantly stimulated ErbB3 phosphorylation.

This Example demonstrates that PEPD induces ErbB2 phosphorylation slowly and transiently, but causes pronounced and persistent ErbB2 depletion. In CHO-K1/ErbB2 cells which stably overexpressed human ErbB2 and human breast cancer BT-474 cells which constitutively overexpressed ErbB2, two key tyrosine phosphorylation sites on ErbB2, pY1221/1222 and pY1196, were measured. ErbB2 tyrosine phosphorylation at both sites was evidently increased after 0.5-1 h of PEPD treatment at 2.7 nM, peaked at 3 h, and largely returned to basal level at 24 h (FIGS. 2a and 2b). At higher PEPD concentrations (27 and 270 nM), ErbB2 tyrosine phosphorylation at these sites increased further and lasted longer (FIG. 2c). The relatively slow ErbB2 tyrosine phosphorylation induced by PEPD is consistent with the relatively slow PEPD binding to ErbB2 monomer and subsequent dimerization (FIG. 1f). PEPD binds to preexisting ErbB2 dimer rapidly (FIG. 1f), but it is known that such dimers are auto-tyrosine phosphorylated. As expected, neither epidermal growth factor (EGF) nor NRG-1 (ligands of other ErbBs) activated ErbB2 in CHO-K1/ErbB2 cells (FIG. 9). In cells treated with PEPD at 2.7 nM, ErbB2 protein level began to decrease at 1 h, reached its lowest level at 6 h, which was sustained for at least 72 h (FIG. 2a), whereas there was no change in ErbB2 level in vehicle-treated cells (FIG. 2b). The impact of PEPD on ErbB2 protein level was dose-dependent, and at 270 nM, PEPD caused almost total ErbB2 elimination (FIG. 2c). To understand how PEPD caused ErbB2 depletion, we measured ErbB2 ECD in the culture medium and ErbB2-p95 (minus ECD) in the cell lysates after CHO-K1/ErbB2 cells were treated with PEPD, since ErbB2 can undergo ECD shedding. 4-Aminophenylmercuric acid (APMA) is known to cause ErbB2 ECD cleavage and, as expected, generated the p95 fragment (minus ECD) in the cell lysates and the ECD in the medium (FIG. 2d). However, even when cells were treated with PEPD at 270 nM for up to 6 h, no ErbB2 ECD shedding occurred (FIG. 2d). Thus, PEPD does not cause ErbB2 ECD cleavage. Also, there was no change in ErbB2 mRNA level in either CHO-K1/ErbB2 cells or BT-474 cells after PEPD treatment for 6 h (FIG. 2e), indicating that PEPD-induced ErbB2 depletion was not due to inhibition of ERBB2 gene expression either. Next, both CHO-K1 cells and CHO-K1/ErbB2 cells were treated with vehicle or PEPD, followed by immunofluorescence staining of ErbB2 and PEPD and detection by confocal microscopy. Cells were treated by PEPD at a high concentration (270 nM) to enhance detection. In CHO-K1 cells, ErbB2 staining was negligible and there was no PEPD staining (FIG. 2f), consistent with very low ErbB2 expression in these cells. In CHO-K1/ErbB2 cells, ErbB2 was strongly stained in the plasma membrane, and after incubation with PEPD for 0.25 h, strong PEPD staining in the plasma membrane was also detected, which co-localized with ErbB2 (FIG. 2f), consistent with PEPD binding to ErbB2. However, in CHO-K1/ErbB2 cells treated with PEPD for 2 h, staining intensity of both proteins in the plasma membrane decreased, with concurrent increase of staining in the cytoplasm (FIG. 2f), suggesting that ErbB2 and PEPD were internalized. ErbB2 was previously shown to undergo clathrin-independent endocytosis, ubiquitination and degradation. Indeed, when cells were treated with PEPD at 2.7 nM for 0.5 h, level of ubiquitinated ErbB2 increased significantly (FIG. 2g).

Example 3

Figure 3:
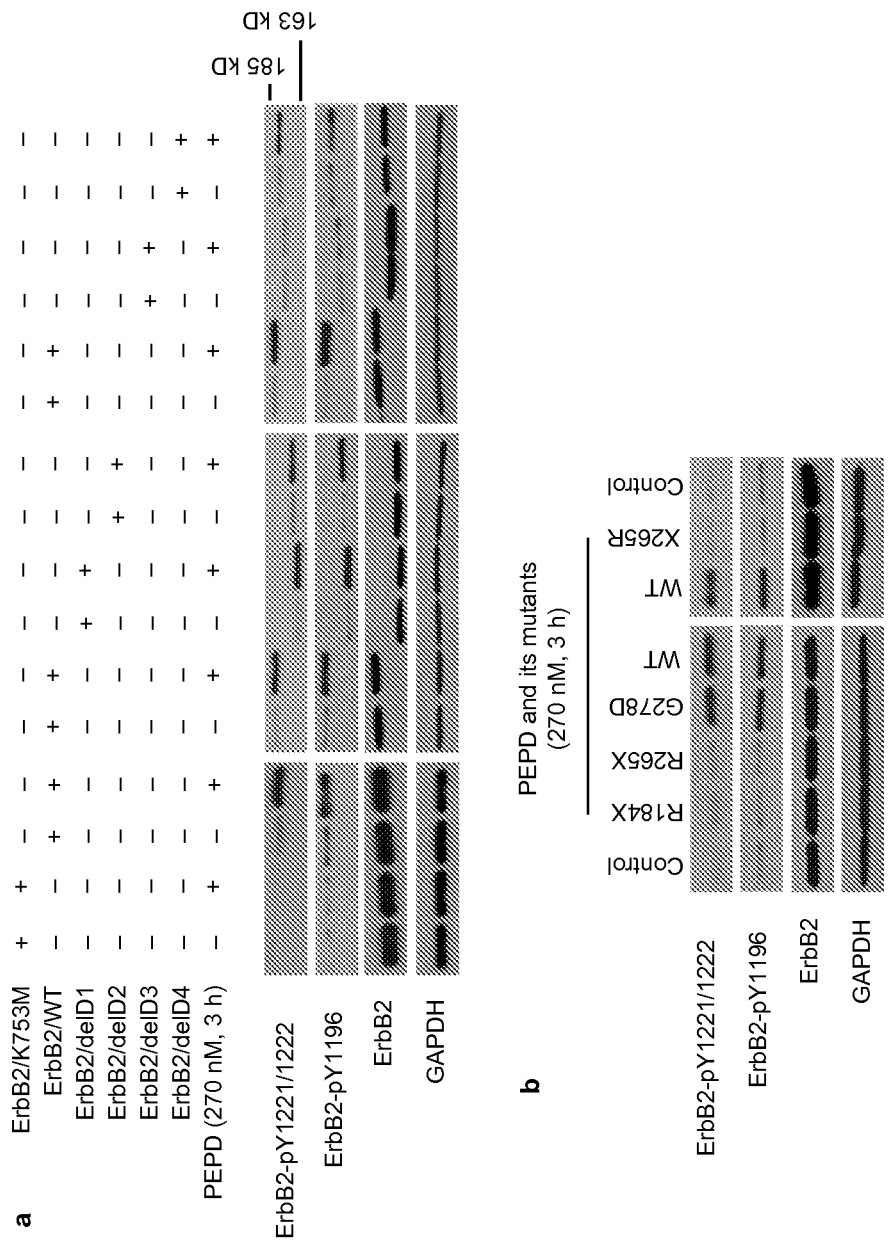
FIG. 3. Data showing PEPD directly activates ErbB2, but its dipeptidase function is not involved. (a) CHO-K1 cells were transfected with ErbB2 or a mutant (all carried by pCMV6-XL5) and 24 h later treated with vehicle or PEPD. Cell lysates were analyzed by western blotting. (b) CHO-K1 cells were transfected with ErbB2 and 24 h later treated with vehicle, PEPD or its mutants. Further information on the mutants is provided in FIG. 10. Cell lysates were analyzed by western blotting.

This Example demonstrates that ErbB2 phosphorylation results from direct PEPD binding, but the dipeptidase function of PEPD is not involved. We analyzed whether stimulation of ErbB2 phosphorylation by PEPD results from direct interaction between the two proteins. First, CHO-K1 cells were transfected with a kinase-dead ErbB2 mutant (K753M) for 24 h and then treated with PEPD at 270 nM for 3 h, a condition shown to cause maximal phosphorylation of wild-type ErbB2. The ErbB2 mutant was overexpressed in the cells after gene transfection, but PEPD failed to stimulate its phosphorylation, whereas under the same experimental condition, PEPD stimulated the phosphorylation of the wild-type ErbB2 (FIG. 3a). Next, CHO-K1 cells were transfected with the ErbB2 mutants lacking an ECD subdomain (FIG. 1d) for 24 h and then treated with PEPD at 270 nM for 3 h. PEPD-induced ErbB2 phosphorylation at both pY1221/1222 and pY1196 in both ErbB2/delD1 and ErbB2/delD2 was comparable to that in WT-ErbB2, absent in ErbB2/delD3, and attenuated in ErbB2/delD4 (FIG. 3a), which correlated well with PEPD binding to these mutants (FIG. 1e). These results suggest that ErbB2 activation by PEPD in cells results entirely from direct binding of PEPD to ErbB2.

Figure 10:
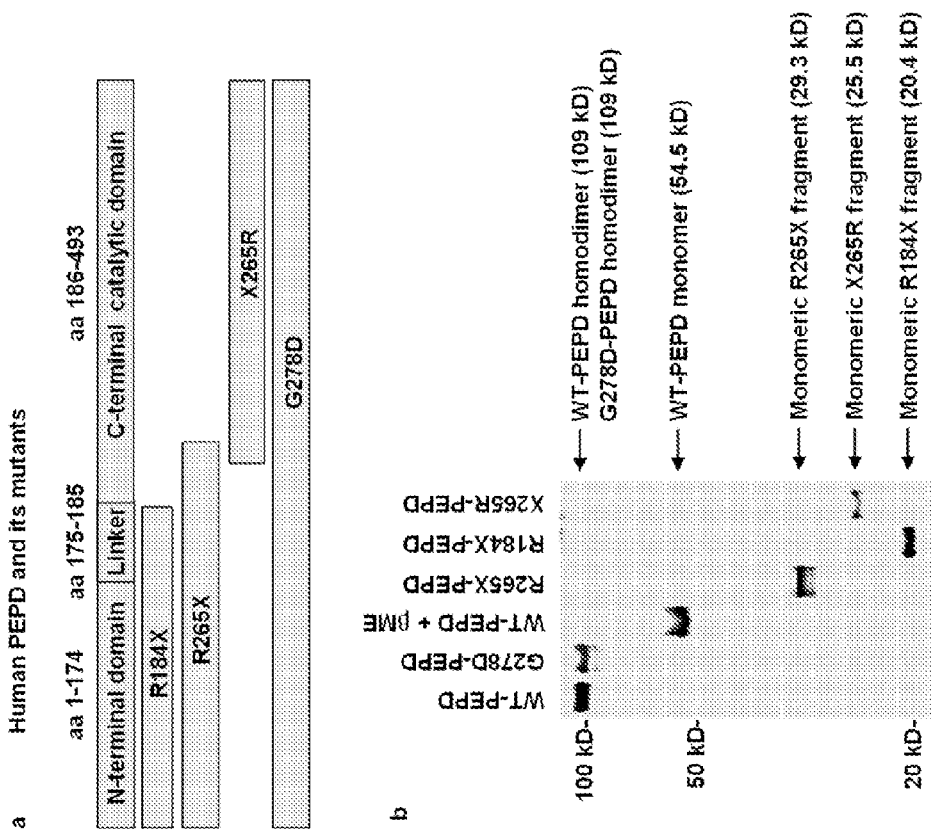
FIG. 10. Data showing configuration of human PEPD and its mutants. (a) Wild-type human PEPD and amino acid (aa) changes in its mutants. (b) Recombinant wild-type human PEPD and its mutants were generated in bacteria, purified using nickel affinity chromatography and analyzed by non-reducing SDS-PAGE and silver staining. Note: Protein loading varied across the lanes. In the lane indicated by "WT-PEPD+βME", the wild-type PEPD was incubated with 10% β-mercaptoethanol in PBS before non-reducing gel electrophoresis.

Four mutants of human PEPD were generated and evaluated to better understand PEPD as an ErbB2 ligand, including R184X-PEPD (deletion of 309 amino acids from the C-terminus), R265X-PEPD (deletion of 228 amino acids from the C-terminus), G278D-PEPD (G→D at amino acid #278), and X265R-PEPD (deletion of 228 amino acids from the N-terminus) (FIG. 10a). CHO-K1 cells were transfected with wild-type human ErbB2 for 24 h and then treated with wild-type PEPD and each of its mutants at 270 nM for 3 h. The PEPD mutants failed to induce ErbB2 phosphorylation, except G278D-PEPD which was identical to WT-PEPD in activating ErbB2 (FIG. 3b). However, G278D-PEPD is enzymatically inactive (see, e.g., Ledoux P, et al. Expression and molecular analysis of mutations in prolidase deficiency. Am J Hum Genet 1996; 59: 1035-1039.) Interestingly, only WT-PEPD and G278D-PEPD could form homodimers (FIG. 10b). Thus, the dipeptidase activity of PEPD is not involved in ErbB2 activation, but homodimerization of PEPD likely is required for PEPD to bind and activate ErbB2.

Figure 11:
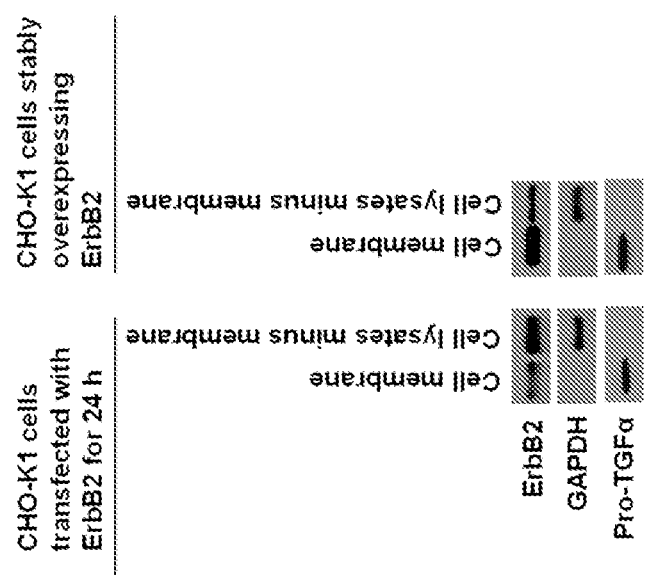
FIG. 11. Data showing ErbB2 distribution in cells. Membrane fraction and lysates minus membrane were prepared from CHO-K1 cells that either stably overexpressed human ErbB2 (CHO-K1/ErbB2 cells) or were transiently transfected with ErbB2 (pCMV6-XL5-ERBB2) for 24 h, and were analyzed by western blotting. GAPDH and pro-TGF-α were used as loading controls. Notably, in the experiments described above (see FIG. 3), PEPD or its G278D mutant did not cause decrease in ErbB2 protein level, whereas PEPD caused pronounced ErbB2 depletion in cells stably or constitutively overexpressing ErbB2 (see FIGS. 2a and 2c). We found that in CHO-K1 cells transiently overexpressing ErbB2, the majority of ErbB2 molecules resided intracellularly, whereas in CHO-K1 cells stably overexpressing ErbB2, the majority of ErbB2 molecules were expressed on cell surface, as shown here. This explains why PEPD treatment for 3 h did not cause clear ErbB2 protein decrease in cells transiently overexpressing ErbB2 (see FIG. 3).

Notably, in the experiments described above, PEPD or its G278D mutant did not cause decrease in ErbB2 protein level, whereas PEPD caused pronounced ErbB2 depletion in cells stably or constitutively overexpressing ErbB2 (FIGS. 2a and 2c). We found that in CHO-K1 cells transiently overexpressing ErbB2, the majority of ErbB2 molecules resided intracellularly, whereas in CHO-K1 cells stably overexpressing ErbB2, the majority of ErbB2 molecules were expressed on cell surface (FIG. 11). This may explain why PEPD treatment for 3 h did not cause a clear ErbB2 protein decrease in cells transiently overexpressing ErbB2.

Example 4

Figure 4:
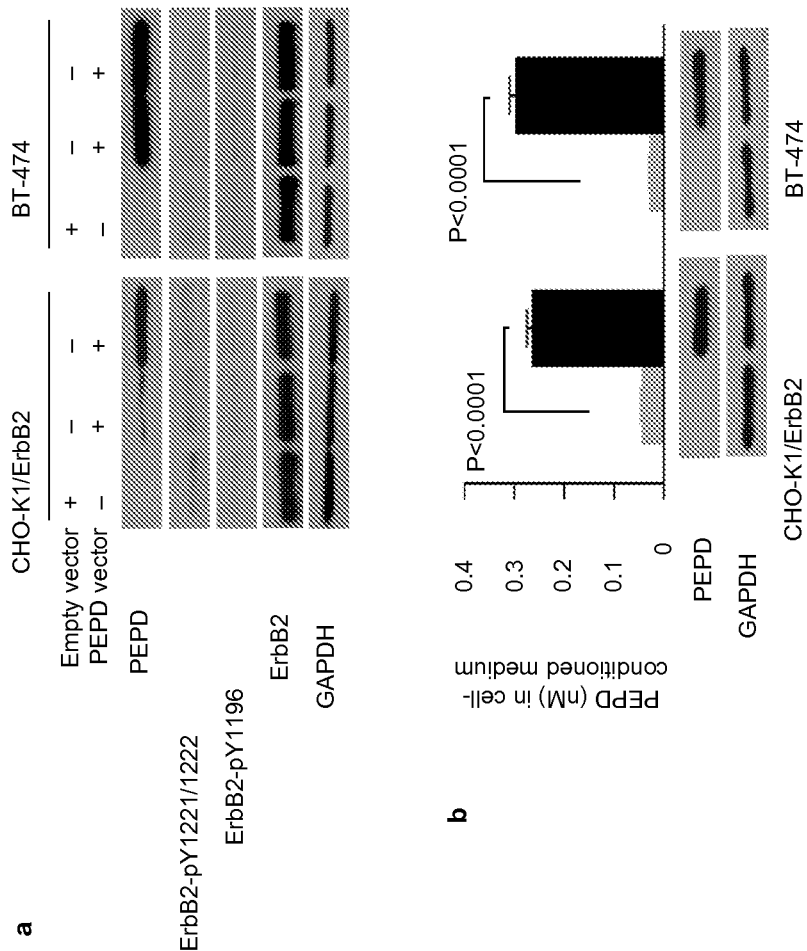
FIG. 4. Data showing lack of effect of intracellular PEPD on ErbB2, but PEPD is released from cell. (a) Cells were transfected with a plasmid expressing human PEPD (pCMV6-XL5-PEPD) or the empty vector for 24 h. Cell lysates were analyzed by western blotting. (b) Cells were transfected with human PEPD or the empty vector; 24 h later, the cells were washed and cultured in fresh medium ($\sim 1 \times 10^6$ cell/2 ml medium) for another 24 h, followed by collection of both cells and the medium. PEPD levels in the cell lysates were measured by western blotting, and PEPD concentration in the medium was measured by ELISA (n=3). Error bars indicate SD.

This Example demonstrates that intracellular PEPD does not modulate ErbB2. PEPD is mainly a cytosolic protein. Endogenous PEPD levels in CHO-K1/ErbB2 cells and BT-474 cells were relatively low, but PEPD level could be readily elevated in these cells via gene transfection. Modest or strong PEPD overexpression was detected at 24 h after transfection of a plasmid expressing human PEPD, but neither ErbB2 tyrosine phosphorylation nor ErbB2 protein expression changed following PEPD overexpression (FIG. 4a). To find out whether cells release PEPD, PEPD-overexpressing cells and control cells were cultured in medium for 24 h, followed by measurement of PEPD level in the cell lysates by western blotting and in the media by ELISA. PEPD concentrations in the media of PEPD-overexpressing cells were 5.9 fold (CHO-K1/ErbB2 cells) and 10.3 fold (BT-474 cells) higher than in the media of the control cells (FIG. 4b). Because all cells appeared morphologically normal and healthy, the above result suggests that PEPD may be actively released by the cells. However, due to apparently excessive dilution by the culture medium, extracellular PEPD concentration was too low (<0.3 nM) to impact ErbB2 (FIG. 4b).

Example 5

Figure 12:
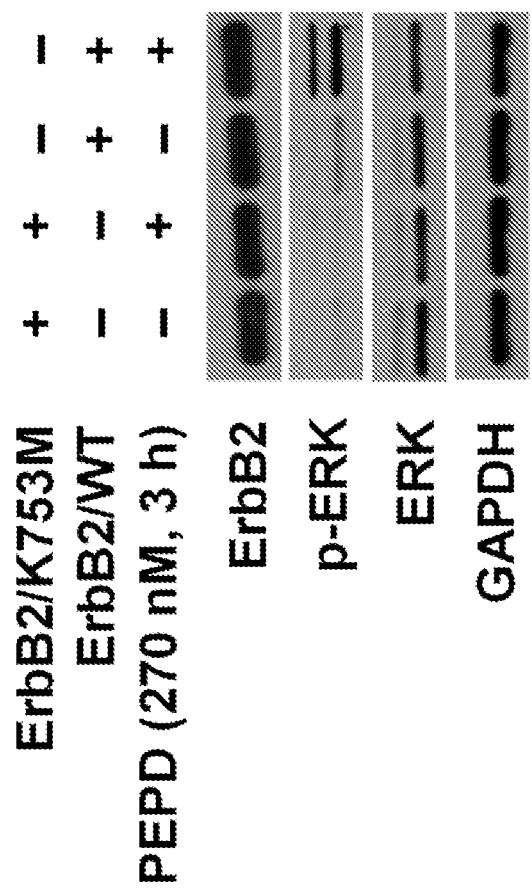
FIG. 12. Data showing that induction of ERK phosphorylation by PEPD in CHO-K1 cells depends on ErbB2. CHO-K1 cells were transiently transfected with wild-type human ErbB2 or a kinase-dead mutant (ErbB2/K753M) for 24 h and then treated with PEPD or vehicle, followed by western blotting.
Figure 13:
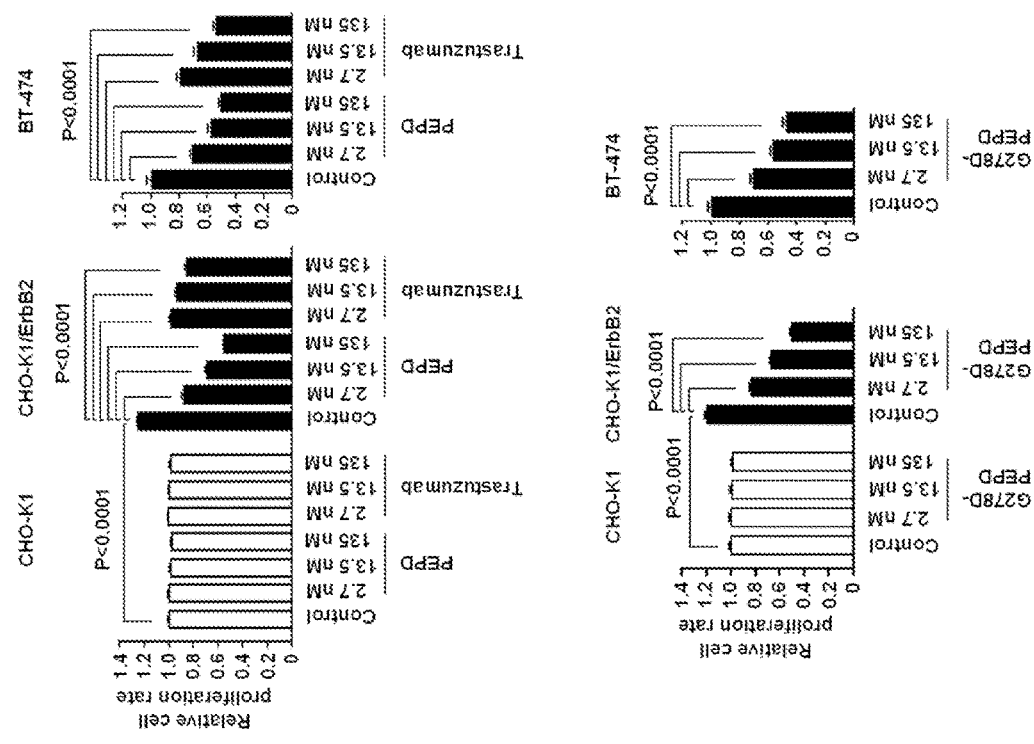
FIG. 13. Data showing the growth-inhibitory effects of PEPD, G278D-PEPD and trastuzumab on cells with or without ErbB2 overexpression. Cells were grown in 96-well plates (500 CHO-K1 cells or CHO-K1/ErbB2 cells per well or 2,000 BT-474 cells per well; 150 μl medium per well) overnight and then treated with vehicle, PEPD, G278D-PEPD or trastuzumab in 200 μl medium per well for 72 h, followed by incubation with methylthiazolyldiphenyl-tetrazolium bromide (MTT) (9.2 mM in medium) at 37° C. for 3 h. After removing the medium, the cells were treated with dimethyl sulfoxide (150 μl per well), and the cell density was determined by measuring formazan formed from MTT spectroscopically at 570 nm (n=3). The error bars indicate SD.

This Example demonstrates that PEPD rapidly silences ErbB2-Src signaling. ERK lies downstream of ErbB2. As expected, PEPD treatment (2.7 nM) led to ERK activation in a time frame which coincided with that of ErbB2 phosphorylation (compare FIG. 5a with FIG. 2a), suggesting rapid signal transmission from activated ErbB2 to ERK. Indeed, in CHO-K1 cells expressing the kinase-dead ErbB2 mutant K753M, PEPD caused neither ErbB2 phosphorylation (FIG. 3a) nor ERK phosphorylation (FIG. 12). AKT also lies downstream of ErbB2, but its S473 phosphorylation, which is critical for its function, was reduced by PEPD (2.7 nM) in both CHO-K1/ErbB2 cells and BT-474 cells in a time-dependent manner (FIG. 5a), whereas vehicle treatment had no impact on AKT phosphorylation (FIG. 5b). This suggested that PEPD modulated ErbB2 signaling via additional mechanisms. As mentioned before, ErbB2 overexpression causes spontaneous dimerization and auto-tyrosine phosphorylation. It is also known that Src and PI3K are activated when bound to tyrosine-phosphorylated ErbB2 homodimers or heterodimers, which lead to activation of AKT. In CHO-K1/ErbB2 cells, ErbB2 associated with Src along with CK2, a Src substrate and a pleiotropic serine/threonine protein kinase, but PI3K was not detected, whereas in BT-474 cells, ErbB2 associated with Src, CK2 and PI3K (FIG. 5c). Treatment of these cells with PEPD (2.7 nM) for only 0.5 h led to marked dissociation of Src and CK2 from ErbB2, but PI3K remained associated with ErbB2 (FIG. 5c). Accordingly, Src kinase activity was significantly attenuated by PEPD in both CHO-K1/ErbB2 cells and BT-474 cells, while PI3K activity remained unchanged (FIG. 5d). However, neither Src nor PI3K was significantly modulated by PEPD in CHO-K1 cells (FIG. 5d). Further experiments showed that Src phosphorylation at Y419, critical for its kinase function, decreased significantly in both CHO-K1/ErbB2 cells and BT-474 cells after treatment with PEPD (2.7 nM) for only 10 min (FIG. 5e), indicating rapid PEPD binding to ErbB2 dimers and rapid disruption of the ErbB2-Src signaling unit. Given that the impact of PEPD on Src occurred before a clear change in ErbB2 phosphorylation and expression, particularly in CHO-K1/ErbB2 cells (FIG. 2a), PEPD likely altered the conformation of preexisting ErbB2 dimers, causing Src disassociation from ErbB2.

PEPD-induced suppression of Src and CK2 was accompanied by loss of PTEN phosphorylation at S380 (FIG. 5a), compared to vehicle-treated controls (FIG. 5b). PTEN phosphorylation at this site by CK2 is known to contribute to the inhibition of PTEN activity. It is also known that PTEN dephosphorylates membrane-bound PIP3, thereby inhibiting AKT phosphorylation and that Src also prevents PTEN translocation to plasma membrane by directly phosphorylating PTEN on tyrosine residues. Indeed, PEPD (2.7 nM, 0.5 h) inhibited PTEN tyrosine phosphorylation in both CHO-K1/ErbB2 cells and BT-474 cells (FIG. 5f), and PTEN translocation from cytoplasm to plasma membrane increased after PEPD treatment (2.7 nM, 1 h) (FIG. 5g).

Example 6

This Example demonstrates that PEPD targets cells overexpressing ErbB2. Our finding of PEPD binding to ErbB2 and the ensuing changes is summarized in FIG. 6a. The rapid inhibition of Src which plays a major role in ErbB2 oncogenesis along with strong ErbB2 depletion suggested that PEPD might inhibit cells overexpressing ErbB2. The potential inhibitory effects of PEPD on CHO-K1 cells, CHO-K1/ErbB2 cells and BT-474 cells were evaluated using three assays as described below.

The effect of PEPD on DNA synthesis was measured by BrdU incorporation via flow cytometry. Cells were treated by PEPD at 2.7 and 27 nM for 48 h. While PEPD was ineffective in CHO-K1 cells, it reduced the number of BrdU-positive CHO-K1/ErbB2 cells and BT-474 cells by up to 65% and 50%, respectively (FIG. 6b). To measure the effect of PEPD on anchorage-independent growth, cells were grown in soft agar and treated with PEPD at 2.7 and 27 nM for 21 days with medium change of every 3-4 days. Colony formation was not significantly affected by PEPD in CHO-K1 cells but was markedly inhibited by PEPD in both CHO-K1/ErbB2 cells and BT-474 cells. PEPD reduced the number of colonies with diameter of ≥100 μm in CHO-K1/ErbB2 cells and BT-474 cells by up to 50% and 57%, respectively (FIG. 6c). The effect of PEPD on cell invasion and migration was measured using BD BioCoat Matrigel Invasion Chambers. Cells were grown in the upper chamber and treated with solvent or PEPD at 2.7 and 27 nM for 48 h, and the cells that invaded through the Matrigel membrane at the bottom of the upper chamber were counted. PEPD was ineffective in CHO-K1 but inhibited the invasion and migration of CHO-K1/ErbB2 cells and BT-474 cells by up to 50% and 51%, respectively (FIG. 6d). Collectively, these results confirm that the impact of PEPD on ErbB2 is predominantly inhibitory and also show that PEPD selectively targets cells overexpressing ErbB2.

It will be apparent from the foregoing data that the present disclosure breaks the long spell of ErbB2 being believed to be an orphan receptor. Compared to other ligands of ErbB receptors, several unusual characteristics of human PEPD are notable: it does not have an EGF motif; it apparently binds to ErbB2 as a homodimer; and it suppresses the oncogenic signaling of ErbB2. PEPD binds to both ErbB2 monomer and ErbB2 dimer, but as shown in FIG. 1f, PEPD binds to ErbB2 homodimers more rapidly than to ErbB2 monomers. This explains why PEPD causes vary rapid disruption of ErbB2-Src signaling (FIG. 5) but somewhat slow ErbB2 phosphorylation (FIG. 2a).

Figure 5:
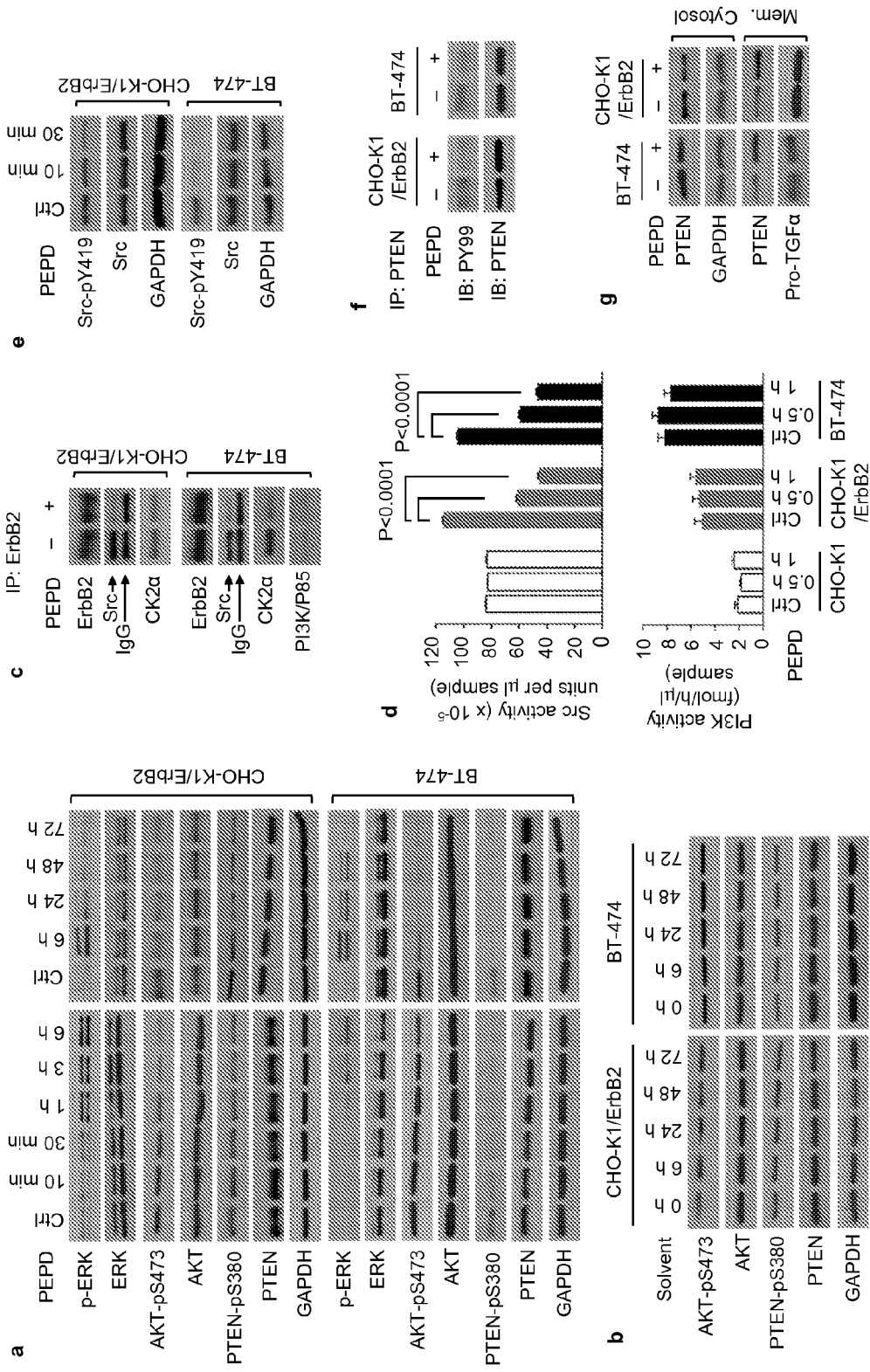
FIG. 5. Data showing that PEPD silences ErbB2-Src signaling. (a, b) Cells were treated with solvent or PEPD (2.7 nM). Cell lysates were analyzed by western blotting. (c) Cells were treated with or without PEPD (2.7 nM, 0.5 h). Cell lysates were incubated with an ErbB2 antibody, pulled down with protein G-agarose, and analyzed by western blotting. (d) Cells were treated with or without PEPD (2.7 nM) and then measured for Src kinase activity and PI3K activity in the cell lysates (n=3). Error bars indicate SD. (e) Cells were treated with or without PEPD (2.7 nM). Cell lysates were analyzed by western blotting. (f) Cells were treated with pervanadate (30 μM, 10 min) and then treated with or without PEPD (2.7 nM, 0.5 h). Cell lysates were incubated with a PTEN antibody, pulled down with protein G-agarose, and analyzed by western blotting. (g) Cells were treated with solvent or PEPD (2.7 nM, 1 h); cytosolic fraction and membrane fraction were prepared and analyzed by western blotting. Both GAPDH and pro-TGFα were used as loading controls.
Figure 14:
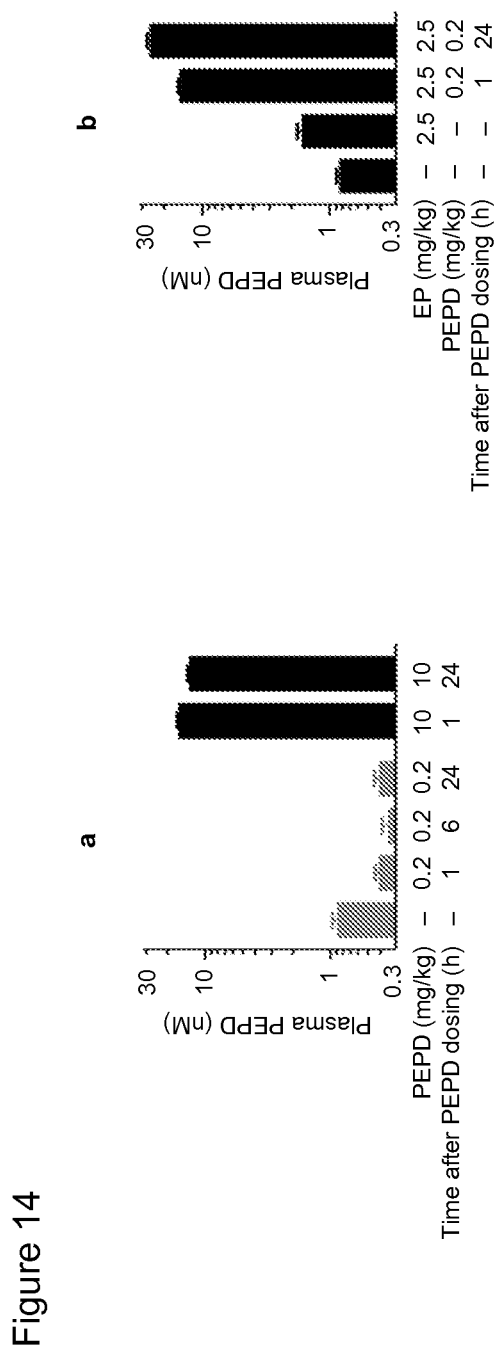
FIG. 14. Data showing the impact of a blood coagulation inhibitor on plasma levels of PEPD. (a) Recombinant human PEPD was administered to mice by intraperitoneal injection at 0.2 mg/kg body weight or 10 mg/kg; mice were killed at 1, 6 or 24 h after PEPD dosing, and plasma level of PEPD was measured by ELISA along with that in the control mice. (b) Enoxaparin (EP), a blood coagulation inhibitor, was administered to mice by intraperitoneal injection at 2.5 mg/kg once daily; 1 h after the fourth EP dose, PEPD was administered to the mice by intraperitoneal injection at 0.2 mg/kg; mice were killed 1 or 24 h after PEPD dosing, and plasma PEPD level was measured by ELISA along with that in the control mice. Each value is a mean±SD. The result shows that EP helps elevate plasma PEPD level by at least 50 fold.

When evaluated for its effect on cell growth and proliferation, PEPD was ineffective in CHO-K1 cells that expressed a low level of ErbB2 but showed strong inhibitory activities in ErbB2-overexpressing CHO-K1 cells (CHO-K1/ErbB2 cells) and BT-474 cells, including inhibition of DNA synthesis, anchorage-independent growth, and invasion and migration (FIGS. 6b-6d). This shows that PEPD targets ErbB2 oncogene addiction, as CHO-K1/ErbB2 cells were derived from CHO-K1 cells; at least two mechanisms may be involved: PEPD causes ErbB2 depletion by inducing ErbB2 internalization and degradation, and PEPD inhibits ErbB2-Src signaling by disrupting their association (FIG. 5). The effects of PEPD on ErbB2 resemble that of trastuzumab, an ErbB2-targeting monoclonal antibody which binds to subdomain 4 of ErbB2 ECD and is used currently for treating ErbB2-positive breast cancers. Data presented in the foregoing examples show that at equimolar concentrations, inhibition of proliferation of CHO-K1/ErbB2 cells and BT-474 cells by PEPD or its G278D mutant was similar to, if not better than that by trastuzumab, while none of the agents showed inhibitory activity in CHO-K1 cells (FIG. 14). Recombinant human PEPD or its mutant, produced in bacteria, may potentially be a low cost alternative to the highly expensive trastuzumab which must be produced in mammalian cells. Moreover, as mentioned before, in vivo, trastuzumab neither down regulates ErbB2 expression nor inhibits ErbB2 tyrosine phosphorylation in cancer tissues; rather, its antitumor activity depends mainly on antibody-dependent cell-mediated cytoxicity (ADCC) via its Fc domain. Thus, PEPD or its mutant may synergizes with trastuzumab or overcome to certain extent the resistance to trastuzumab in patients. PEPD does not bind to ErbB3 and ErbB4 (FIG. 1a), but it is well known that ErbB2 is a preferred heterodimerization partner with these ErbBs. This raises the question of whether blockade of ErbB2 oncogenic signaling by PEPD may also include inhibition of ErbB2 heterodimer signaling units. Notably, in human breast cancer, the oncogenic activity of ErbB2 depends critically on ErbB3. It will be apparent to those skilled in the art that the present disclosure reveals a fundamentally new function of human PEPD: an ErbB2 ligand independent of its dipeptidase activity. PEPDs from many species share high sequence homology with human PEPD and may also bind and modulate ErbB2.

In view of in vitro results described in Examples 1-6, which strongly support the use of PEPD as an agent for treating Erb2 positive cancers, we tested PEPD and the enzymatically inactive version of it in vivo to determine its efficacy against ErbB2 positive cancers in clinically relevant animal models, as described in the following Examples.

Example 7

This Example demonstrates using recombinant human PEPD and its mutant PEPD$^{G278D}$ in vivo as an anticancer agent. As was the case in the in vitro experiments shown in Examples 1-6, the data presented in this example were obtained using recombinant human PEPD and its mutant PEPD$^{G278D}$ with 6×His tagged to the carboxy terminus that were generated in *E. coli* and purified by affinity chromatography using a HIS tag engineered into these proteins. These products were used in the following experiments.

Figure 15:
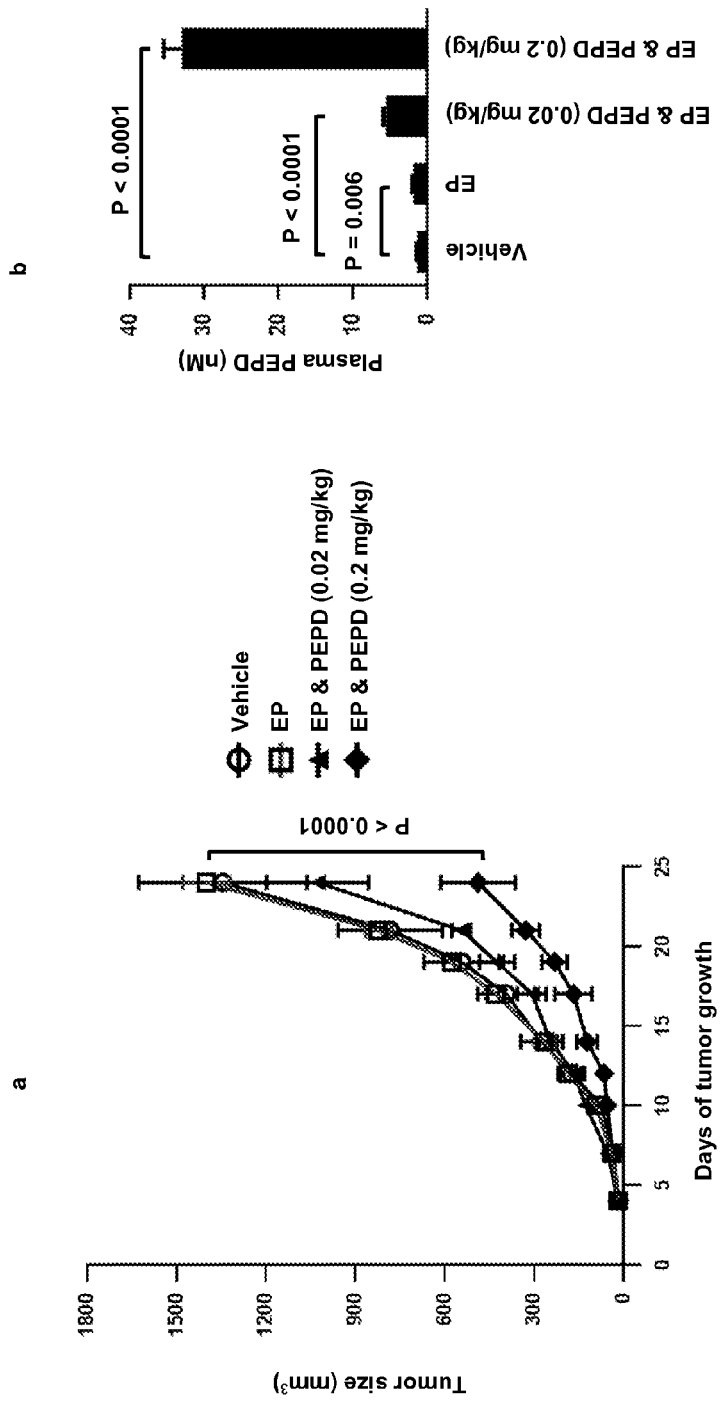
FIG. 15. Data showing the effects of PEPD and coagulation inhibitor EP in vivo. CHO-K1/ErbB2 cells were inoculated subcutaneously to the flanks of female athymic nude mice (6-7 weeks of age) at $1 \times 10^6$ cells per site in a small volume of PBS:Matrigel mix. Starting 4 days after cell inoculation, the mice were given either vehicle or enoxaparin (EP) at 2.5 mg/kg by intraperitoneal injection once daily. After 3 days of EP treatment (day 7 after cell inoculation), when tumor volume reached approximately 41 mm$^3$, a subset of EP-treated mice were also treated with PEPD at 0.02 mg/kg or 0.2 mg/kg by intraperitoneal injection, which was given three times per week (Monday, Wednesday, Friday). On the days when both EP and PEPD were given, PEPD was given 1 h after EP. Tumor volume was measured three times per week (Monday, Wednesday, Friday). The mice were killed 24 h after the last treatment (on day 24 after cell inoculation, and a total of 8 PEPD treatments), and blood samples were collected from the mice for measurement of plasma level of PEPD by an ELISA assay. (a) Each value is a mean±SEM (n=8-11). (b) Each value is mean±SD (n=3). PEPD strongly inhibited tumor growth but EP had no effect.

First, we carried out dose-finding experiments. In vitro, PEPD at concentrations as low as 2.7 nM was effective against ErbB2-overexpressing cells. Adult C57BL/6 mice were given a single intraperitoneal dose of PEPD, and mice were killed for blood collection at 1, 6 or 24 h post dosing. While giving PEPD at 10 mg/kg elevated plasma PEPD to 16.5 nM at 1 h and 13.6 nM at 24 h post dosing, compared to 0.9 nM in the control mice, giving PEPD at 0.2 mg/kg unexpectedly resulted in 51-61% decrease in plasma PEPD level (FIG. 14a). However, we discovered that combining the PEPD agents with enoxaparin (EP), which is a clinically used small molecular weight heparin and is known to inhibit factor Xa and other coagulation factors, results in persistence of PEPD, as plasma level of PEPD following PEPD dosing at 0.2 mg/kg were up to 64 fold higher in EP-pretreated mice than in mice without EP treatment (FIG. 14b). Without intending to be constrained by any particular theory, it is believed that the EP may be reducing degradation of the PEPD. It is plausible that other coagulation inhibitors will also be effective in maintaining PEPD plasma concentration in vivo. Next, we analyzed whether PEPD inhibits the growth of ErbB2-overexpressing tumors in vivo. CHO-K1/ErbB2 cells, which stably overexpress human ErbB2 but do express any other ErbB family receptors, were inoculated subcutaneously to the flanks of female athymic nude mice (6-7 weeks of age) at 1×10$^6$ cells per site in a small volume of PBS:Matrigel mix. Starting 4 days after cell inoculation, the mice were given either vehicle or EP at 2.5 mg/kg by intraperitoneal injection once daily. Three days after EP treatment was started (on day 7 after cell inoculation), when tumor volume reached approximately 41 mm$^3$, the EP-treated mice were also treated with vehicle or PEPD at 0.02 mg/kg or 0.2 mg/kg by intraperitoneal injection, which was given three times per week (Monday, Wednesday, Friday). Notably, on the days when both EP and vehicle/PEPD were given, vehicle or PEPD was always given 1 h after EP dosing. Tumor volume was measured three times per week (Monday, Wednesday, Friday) by length×width$^2$/2. The mice were killed 24 h after the last treatment which was given on day 24 after cell inoculation (a total of 8 PEPD treatments), and blood samples were collected from the mice for measurement of plasma levels of PEPD by ELISA. While EP had no effect on tumor growth, EP plus PEPD at 0.02 and 0.2 mg/kg inhibited tumor growth by 27% (statistically insignificant) and 65% (highly statistically significant), respectively (FIG. 15a). Plasma levels of total PEPD (endogenous mouse PEPD plus human PEPD) at the end of the experiment were 1.9 nM in EP only group, 5.5 nM in EP plus low dose PEPD group, and 33.0 nM in EP plus high dose PEPD group, which are 1.4-, 4.2-, 24.8-fold higher than in the control mice (FIG. 15b).

Figure 16:
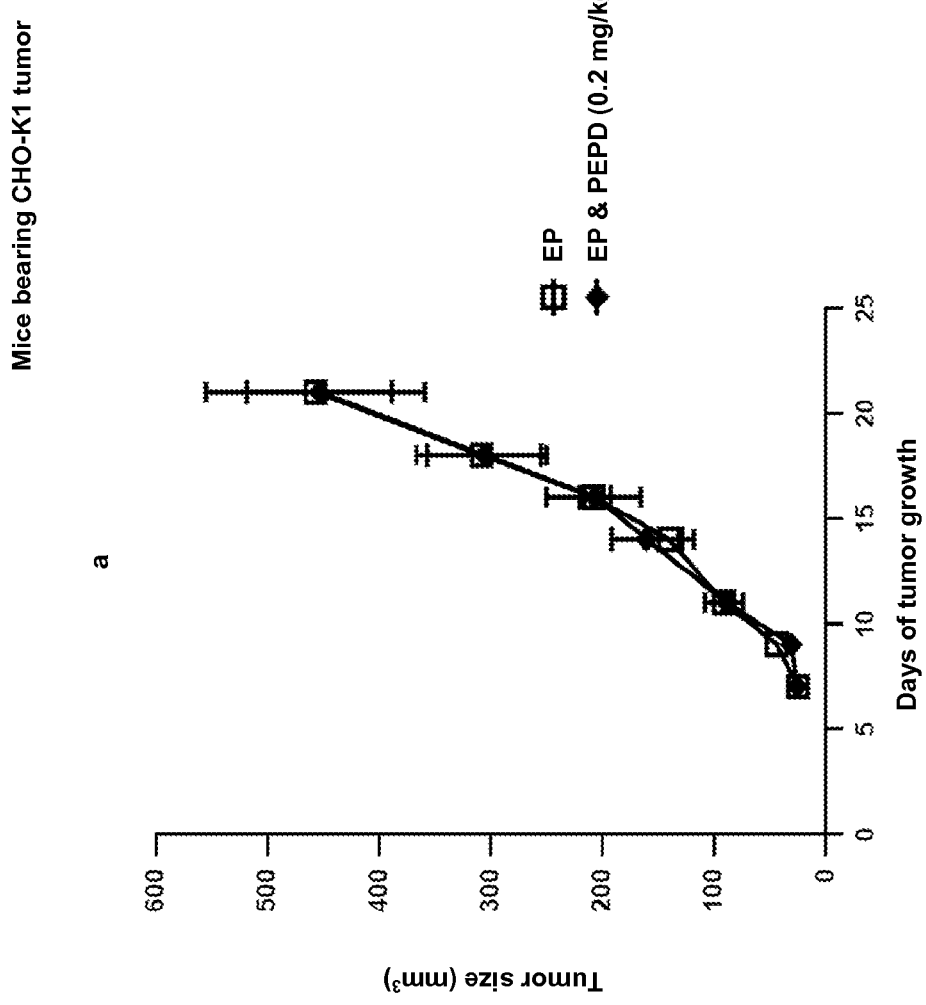

We next analyzed whether PEPD specifically targets ErbB2-overexpressing tumors in vivo. CHO-K1 cells which express negligible ErbB2 and do not express other ErbBs were inoculated subcutaneously to the flanks of female athymic nude mice (6-7 weeks of age) at 1×10$^6$ cells per site in a small volume of PBS; Matrigel mix. Starting 4 days after cell inoculation, the mice were treated with EP at 2.5 mg/kg by intraperitoneal injection once daily. Three days later (on day 7 after cell inoculation), when the tumor volume reached approximately 26 mm$^3$, the mice were also treated with vehicle or PEPD at 0.2 mg/kg by intraperitoneal injection, which was given three times per week (Monday, Wednesday, Friday). On the days when both EP and PEPD/vehicle were given, PEPD/vehicle was always given 1 h after EP administration. Tumor volume was measured three times per week (Monday, Wednesday, Friday). The mice were killed 24 h after the last treatment which was given on day 21 after cell inoculation (a total of 7 PEPD treatments), and blood samples were collected from the mice for measurement of plasma level of PEPD. PEPD treatment had no effect on tumor growth (FIG. 16a), even though plasma levels were elevated as expected (FIG. 16b). Thus, our data presented herein demonstrates that PEPD specifically targets tumors comprising cells which overexpress ErbB2.

Next, the effect of PEPD was evaluated in an orthotopic breast tumor model. Human breast cancer BT-474 cells constitutively overexpress ErbB2 and have been widely used to generate orthotopic breast tumors for evaluation of anti-ErbB2 therapies. Female athymic nude mice (6-7 weeks of age) were each implanted subcutaneously with a 60-day release of 17β-estradiol pellet (1.7 mg of estradiol, purchased from Innovative Research of American) prior to orthotopic inoculation of BT-474 cells into the mammary fat pads ($2\times10^6$ cells per site in a small volume of PBS:Matrigel mix). Twenty three days after cancer cell inoculation, all mice began daily treatment of EP at 0.5 mg/kg daily by intraperitoneal injection. Notably, a dose-finding experiment showed EP at 0.5 mg/kg was as effective as 2.5 mg/kg in maintaining PEPD concentration in the blood. Also, another group of mice that were implanted with 17β-estradiol and then inoculated with BT-474 cells were kept as a no-treatment control, in order to confirm that EP itself did not have any effect on tumor growth. The no-treatment mice were kept for 58 days after cancer cell inoculation (FIG. 17a). The EP-treated mice were randomized to three groups to receive vehicle, PEPD, and PEPD$^{G278D}$, while daily EP treatment continued Based on our experience with PEPD in the CHO-K1/ErbB2 tumor model, we decided to treat mice with PEPD or its mutant at 2 mg/kg. Treatment with vehicle, PEPD or its mutant was started 4 days after the start of EP treatment (on day 27 after cancer cell inoculation), and each was given by intraperitoneal injection three times per week (Monday, Wednesday, Friday). When EP was also given on the same day, it was always given 1 h earlier than the other agent. Tumor volume was measured on Monday, Wednesday and Friday every week. As shown in FIG. 17a, EP had no effect on tumor growth, but both PEPD and PEPD$^{G278D}$ rapidly caused tumor shrinkage. PEPD$^{G278D}$ was more effective than PEPD (the difference in tumor volume between the two groups is statistically significant). In view of the strong antitumor efficacy of the agents, all treatments were stopped 1 month later (last dose was given on day 58 after cancer cell inoculation), and the mice were kept for observation. A small volume of blood was also obtained from the mice 24 h after the last dose for measurement of plasma PEPD level. Plasma PEPD level in mice treated with EP only was 1.9 nM, 1.4-fold higher than in mice with no treatment (FIG. 17b), again showing that EP significantly facilitates persistence of endogenous mouse PEPD. Moreover, plasma PEPD levels in the mice treated with EP plus PEPD and EP plus PEPD$^{G278D}$ were 154.3 nM and 128.6 nM, respectively, which are 111.0- and 92.5-fold higher than in mice with no treatment (FIG. 10b). A second 17β-estradiol pellet was implanted to each mouse on day 59 after cancer cell inoculation. Three weeks after treatment stop (on day 80 after cancer inoculation), tumors in some mice that were previously treated with PEPD or its mutant regrew. However, 50% of the mice treated with PEPD$^{G278D}$ remained tumor-free and 27% of the mice treated with PEPD remained tumor-free (FIG. 17a), another indication that PEPD$^{G278D}$ is more effective than PEPD. All mice with tumor regrowth were retreated with EP plus PEPD$^{G278D}$: Daily EP at 0.5 mg/kg by intraperitoneal injection was started on day 89 after cancer cell inoculation, and PEPD$^{G278D}$ was administered at 2 mg/kg by intraperitoneal injection every other day for a total of 4 doses. As described before, on days when both EP and PEPD$^{G278D}$ were given, EP was given 1 h earlier. The experiment was terminated 24 h after the last PEPD$^{G278D}$ dose. As shown in FIG. 17a, all tumors were still exquisitely sensitive to PEPD$^{G278D}$, indicating that tumor regrowth was not due to the presence of cancer cells that were resistant to PEPD or PEPD$^{G278D}$, but rather it was due to incomplete initial eradication of cancer cells. In addition, the mice previously treated with EP only were re-treated with EP at 0.5 mg/kg once daily, which was started on day 82 after cancer cell inoculation, and 4 days later, the mice were divided into two groups: vehicle treatment or treatment with PEPD$^{G278D}$ at 2 mg/kg, which were given three times per week (Monday, Wednesday, Friday) by intraperitoneal injection for a total of 5 doses. The experiment was terminated 24 h after the last dose. As shown in FIG. 17a, PEPD$^{G278D}$ caused rapid shrinkage of tumor volume, even though the tumors were extremely large at the beginning of the treatment. It is also important to note that the significant antitumor efficacy of PEPD and PEPD$^{G278D}$ was not associated with any toxicity: no effect on mouse body weight gain or the weight of the organs such as colon, heart, kidney, liver, lung and stomach. This indicates that the agents at the therapeutically effective doses are not toxic.

Example 8

This Example provides a demonstration of making a PEPD-Fc hybrid (fusion) protein.

Trastuzumab, which binds to subdomain 4 in ErbB2 extracellular domain, is the most successful and most widely used anti-ErbB2 agent in breast cancer. However, the overall response rate to trastuzumab remains modest, and primary and secondary resistance remains a clinical challenge. The Fc domain of trastuzumab is critical for its antitumor activity by engaging Fc receptors on immune effector cells and eliciting antibody-dependent cell-mediated cytotoxicity. In fact, a clinical study found that trastuzumab at dose levels used for treating ErbB2-positive breast cancers had no ability to down regulate ErbB2 proteins in the cancer tissues (Gennari R, et al. *Clinical Cancer Research* 2004, 10(17): 5650-5655). Fc is also known to promote blood persistence of antibodies. However, PEPD does not have a Fc domain.

Figure 18:
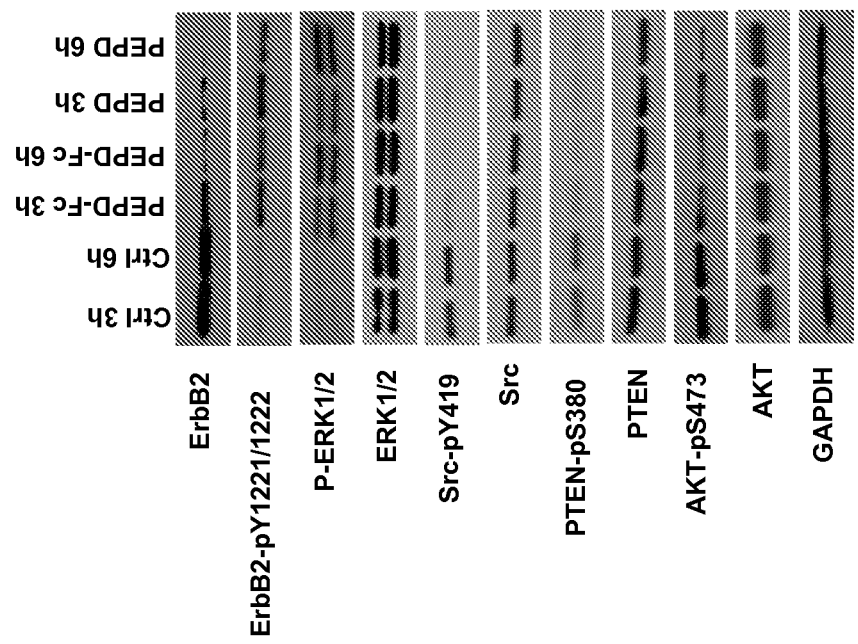
FIG. 18. For comparison of PEPD-Fc with PEPD for impact on ErbB2 and downstream signals, CHO-K1/ErbB2 cells were treated with vehicle, PEPD-Fc (27 nM) or PEPD (27 nM) for 3 or 6 h, followed by western blot analysis. The human PEPD-human Fc hybrid (Fc linked in frame to the carboxyl end of PEPD) was prepared by us using standard recombinant technology.

We conducted tests aiming at making and determining whether adding Fc to PEPD boost its antitumor activity would be plausible. The PEPD-Fc hybrid molecule may also be retained in the blood to a higher level and for a longer time than PEPD is. We have generated PEPD-Fc (monomer molecular weight: 80.9 kD). Briefly, the full coding sequence of human PEPD was subcloned to the pFUSE-hIgG1-Fc vector (InvivoGen), linked in frame at its C terminus to the Fc sequence of human IgG1. The resultant construct (pFUSE-PEPD-Fc) was verified by sequencing and transfected to CHO-K1 cell, and the expressed hybrid protein in the cell lysates was purified using Protein A-Sepharose. High purity of PEPD-Fc was confirmed by SDS-PAGE. The bioactivity of PEPD-Fc was compared to that of PEPD. CHO-K1/ErbB2 cells were treated with vehicle, PEPD-Fc or PEPD (both at 27 nM) for 3 h or 6 h. PEPD-Fc caused time-dependent and significant ErbB2 protein depletion, but was somewhat less effective than PEPD (FIG. 18). It is possible that PEPD-Fc may simply be slightly slower than PEPD in causing ErbB2 depletion, and increasing treatment time may allow PEPD-Fc to achieve the same impact on ErbB2 as PEPD does. Nevertheless, as shown in FIG. 18, the two agents showed very similar impact on ErbB2 phosphorylation and ERK phosphorylation, and on silencing ErbB2-Src signaling (decreasing phosphorylation of Src, PTEN and AKT). Our results indicate that PEPD-Fc largely if not totally retains the ErbB2-modulating activity of PEPD. Given that PEPD-Fc is expected to engage immune cells in vivo, it may be significantly more powerful than PEPD or PEPD$^{G278D}$ in combating ErbB2-positive cancers.

Given the benefit of the present disclosure, PEPD-Fc hybrid and PEPD$^{G278D}$-Fc can be readily evaluated in animal models. In embodiments, these hybrids will be generated in mammalian cells (e.g., CHO-K1 cells) to ensure glycosylation at N297 of Fc, which is essential for Fc function. Interestingly, aglycosylated Fc with certain mutations maintains its bioactivity, including but not limited to $Fc^{T299A}$ and $Fc^{E382V/M428I}$. Thus, additional hybrids with specific mutations to the Fc sequence can be generated, such as in *E. coli* and evaluated using conventional techniques, given the benefit of the present invention.

Example 9

As can be seen from FIG. 17a, and FIGS. 19(a)-(e) which summarize data obtained by measuring in vivo changes in tumors treated by rhPEPD or rhPEPD$^{G278D}$, rhPEPD$^{G278D}$ is superior to rhPEPD with respect to reducing tumor volume in vivo (FIG. 17a and FIG. 19(a)). Without intending to be bound by any particular theory, we believe this is related to the novel discovery that rhPEPD$^{G278D}$ does not stimulate HIF-1α signaling, whereas PEPD does (FIG. 19(e)). In this regard, it is well known in the art that VEGF and GLUT-1 are downstream targets of HIF-1α, and the differing effects on these markers are similar to the effect on HIF-1α. All three are well-known prosurvival factors. However, we also observed that both PEPD and PEPD$^{G278D}$ obliterated ErbB2 signaling, inactivating ErbB3, as well as activating apoptosis in the tumor tissues. Both agents caused ErbB-2 depletion, ErbB2 dephosphorylation (inactivation), dephosphorylation (inactivation) of SRC, AKT, ERK, ErbB3, down regulation of anti-apoptotic Bcl-2, proapoptotic BAX, and activation of multiple caspases in the tumor tissues (FIG. 19b). Both agents also reduced SRC kinase activity and PI3K activity in the tumor tissues (FIG. 19c). We also found both PEPD and PEPD$^{G278D}$ were internalized by tumor cells to similar extent, as measured by their His tag (FIG. 19e). This finding supports the concept that PEPD or PEPD$^{G278D}$ may be conjugated to a toxin or a cancer chemotherapeutic agent, as discussed before, for enhanced anticancer efficacy.

It is notable that in vivo, trastuzumab/herceptin neither down regulates ErbB2 expression nor inhibits ErbB2 tyrosine phosphorylation in cancer tissues (Gennari et al., Clinical Cancer Research, 10, 5650-5655, 2004; Gijsen et al., PLoS Biology, 8, e1000563, 2010). Rather, herceptin relies mainly on antibody-dependent cell-mediated cytoxicity (ADCC). Thus, based on the data presented herein, it is plausible that rhPEPD$^{G278D}$ may complement herceptin or overcome certain herceptin resistance.

Example 10

This Example provides a description of the materials and methods that were used to obtain the data described in Examples 1-9.

Reagents.

Recombinant chimeras, including human ErbB2/ECD-Fc (1129-ER-050), human ErbB3/ECD-Fc (348-RB-050) and human ErbB4/ECD-Fc (1131-ER-050) as well as recombinant Fc of human IgG$_1$ (110-HG-100) were from R&D systems. Recombinant human EGF (236-EG-200) and human NRG-1 (5218) were purchased from R&D Systems and Cell Signaling, respectively. Trastuzumab (Genentech) was obtained from Roswell Park Cancer Institute Pharmacy. 4-Aminophenylmercuric acid (APMA), crystal violet, methylthiazolyldiphenyl-tetrazolium bromide (MTT) and vanadate were from Sigma-Aldrich. The following antibodies were used: anti-PEPD (Abcam, ab86507), anti-PTEN (Santa Cruz, sc-7974), anti-p-PTEN (Santa Cruz, sc-101789), anti-p-Tyr (PY99) (Santa Cruz, sc-7020), anti-CK2a (Santa Cruz, sc-12738), anti-ECD of ErbB2 (Santa Cruz, sc-134481), anti-ErbB3 (Santa Cruz, sc-285), anti-TGFα (Santa Cruz, sc-9043), anti-ErbB2 (Cell Signaling, 2165), anti-p-ErbB2 (Y1196) (Cell Signaling, 6942), anti-p-ErbB2 (Y1221/1222) (Cell Signaling, 2243), anti-ErbB1 (Cell Signaling, 2232), anti-ErbB4 (Cell Signaling, 4795), anti-PI3K p85 (Cell Signaling, 4257), anti-p-Src (Cell Signaling, 6943), anti-Src (Cell Signaling, 2123), anti-AKT (Cell Signaling, 4691), anti-p-AKT (Cell Signaling, 4060), anti-ERK (Cell Signaling, 9102), anti-p-ERK (Cell Signaling, 9101), anti-ubiquitin (Santa Cruz, sc-8017), anti-GAPDH (Millipore, MAB374), anti-human IgG$_1$ for detection of Fc (Santa Cruz, sc-2453), FITC-conjugated anti-His-tag (Abcam, ab1206), biotin-conjugated anti-His-tag (Bethyl, A190-113B), and TRITC-conjugated goat-anti-rabbit (Jackson, 111-025-003). HRP-conjugated streptavidin (N100) was from Thermo Scientific.

Recombinant human PEPD and its mutants (6×His tagged to the carboxy terminus) were generated in bacteria and purified using nickel affinity chromatography (Qiagen). The purity of each protein was confirmed by gel electrophoresis and silver staining (FIG. 10b). Details for the preparation of PEPD and its mutants as well as other reagents are provided below.

The bacterial pBAD/TOPO ThioFusion expression system (Invitrogen) was used to produce and purify PEPD and the PEPD mutants. In brief, pCMV6-XL5-PEPD (Origene) was used as a template to amplify the full length human PEPD by PCR using primers For-5'-AATACGACTCAC-TATAGGGCG-3' (SEQ ID NO:2) and Rev-5'-CTTGGGGC-CAGAGAAGG-3' (SEQ ID NO:3), which were designed to express PEPD as a native protein with 6×His tagged to the carboxy terminus (but without the N-terminal Thio). The resulting PCR fragments were subcloned into the pBAD/Thio-TOPO expression vector by TA cloning. The construct was sequenced to ensure the integrity of the entire coding sequence. Expression and purification were performed as indicated by the manufacturer. The PEPD G278D mutant as well as other mutants, which include the N-terminal 184 amino acids fragment, the N-terminal 265 amino acids fragment, and the C-terminal 265 amino acids fragment, were generated by site-directed mutagenesis using the QuikChange Lightning Multi Site-Directed Mutagenesis kit (Agilent Technologies) and using the above-described PEPD expression vector as the template. The constructs were sequenced to ensure the correct mutation. Both the wild-type PEPD and mutant PEPD were purified via Ni-NTA Agarose Chromatography (Qiagen). The proteins were further purified using Ultracel YM-30 Centricon (Millipore). SDS-PAGE was performed in 8-10% acrylamide gels under denaturing and reducing conditions, and the gels were stained with Silver staining to examine protein purity. The preparations were also checked for potential contamination of lipopolysaccharides, using the E-TOXATE Kit (Sigma), following the manufacturer's instruction, but no lipopolysaccharides were detected (detection limit: 0.005 endotoxin unit per 0.1 ml sample).

Cell Lines and Cell Culture.

BT-474 cells and CHO-K1 cells were from ATCC. CHO-K1/ErbB2 cells were generated by transfecting CHO-K1 cells with pcDNA3-ERBB2 and selected under G418. CHO-K1 cells and CHO-K1/ErbB2 cells were cultured in F-12K medium (Gibco) supplemented with 10% FBS (Gibco). BT-474 cells were cultured in 50% high-glucose DMEM (Mediatech)/50% F-12K medium supplemented with 10% FBS. Human breast cancer MCF-7 cells and human bladder cancer RT-4 cells, from ATCC, were also used in the study. MCF-7 cells and RT-4 cells were cultured in high-glucose DMEM plus 10% FBS and McCoy'SA medium plus 10%

FBS, respectively. All cells were cultured in humidified incubators at 37° C. with 5% $CO_2$.

Gene Transfection and Plasmids.

Cells were grown in 6-well plates and transfected with a plasmid using FuGENE HD (Promega) or Lipofectamine 2000 (Invitrogen). pCMV6-XL5-PEPD expressing wild-type human PEPD was from Origene. pMT107-His-Ub was used to express ubiquitin. pCMV6-XL5-ERBB2 expressing human ErbB2 was generated by cloning full length human ERBB2 coding sequence to the mammalian expression vector pCMV6-XL5 (Origene). To construct pCMV6-XL5-ERBB2 which expresses human ErbB2, the full length human ERBB2 coding sequence was amplified by PCR from the LNCaP cDNA using NotI-forward primer (5'-ATAAGAATGCGGCCGCAGCTGAGATTCCCCTC-CATT-3') (SEQ ID NO:4) and NotI-reverse primer (5'-ATAGTTTAGCGGCCGCCTTGATGCCAGCAGAAGTCA-3') (SEQ ID NO:5). Amplified PCR products were digested by NotI (New England BioLabs), followed by ligation into pCMV6-XL5 (Origene) which was pre-digested with the same restriction enzyme. The orientation of the insert was determined by colony PCR using forward primer 5'-CAAATGGGCGGTAGGCGTGTA-3' (SEQ ID NO:6) (localized to the plasmid) and reverse primer 5'-ATTG-GTGGGCAGGTAGGTGAGTTC-3' (SEQ ID NO:7) (annealed to the beginning of the insert). The construct was sequenced to confirm the integrity of the entire coding sequence. All site-directed mutations and deletions in the ERBB2 gene were performed on pCMV6-XL5-ERBB2, using the QuikChange Lightning Site-Directed Mutagenesis Kit. These constructs include ErbB2 that carries K753M mutation (pCMV6-XL5-ERBB2/K753M), deletion of ErbB2 ECD subdomain 1 (pCMV6-XL5-ERBB2/delD1, deletion of amino acids 1-195), deletion of ErbB2 ECD subdomain 2 (pCMV6-XL5-ERBB2/delD2, deletion of amino acids 196-320), deletion of ErbB2 ECD subdomain 3 (pCMV6-XL5-ERBB2/delD3, deletion of amino acids 321-488), and deletion of ErbB2 ECD subdomain 4 (pCMV6-XL5-ERBB2/delD4, deletion of amino acids 489-560). All constructs were sequenced to ensure the correct mutation/deletion.

Western Blot Analysis.

Preparation of cell lysates, measurement of protein concentration and western blot were performed using standard techniques. Cell membrane, cytosol fractions or cell lysates minus cell membrane were prepared using the Mem-PER Eukaryotic Membrane Protein Extraction Reagent Kit (Thermo Scientific). Cell culture medium was concentrated 20 fold using Centricon (Millipore) before analysis. In experiments measuring the binding of PEPD or NRG-1 to ErbB2 ECD, ErbB3 ECD or ErbB4 ECD, a silver staining kit (Invitrogen) was used to display the proteins after gel electrophoresis. To detect ErbB2 receptor dimerization, PEPD-treated cells and control cells were washed with ice-cold PBS and incubated with cross linker BS3 (Pierce) at 2 mM for 30 min at room temperature. The cross-linking reaction was terminated by adding 50 mM Tris (final, pH7.5), followed by incubation at room temperature for 15 min. Cell lysates were analyzed by western blotting (3.5% SDS-PAGE). Non-reducing gel electrophoresis was used to determine, besides the wild type human PEPD, whether any of its mutants, including G278D-PEPD, R184X-PEPD, R265X-PEPD, and X265R-PEPD, existed as a homodimer. Briefly, each protein sample was mixed with non-reducing sample buffer (sample loading buffer without β-mercaptoethanol) and then resolved by 10% SDS-PAGE, before silver staining. Protein concentrations of all specimens were measured by the Bicinchoninic Acid Assay (BCA) Kit (Pierce).

Immunoprecipitation.

PEPD was incubated with ErbB2/ECD-Fc, ErbB3/ECD-Fc, ErbB4/ECD-Fc or Fc in binding buffer for 2 h at 37° C., followed by pull down with protein G-sepharose beads. The immunoprecipitates were washed with IP washing buffer and analyzed by western blotting. For detection of direct and specific binding of PEPD or NRG-1 to ErbB2, ErbB3 or ErbB4, recombinant human PEPD or NRG-1 was incubated with recombinant human ErbB2/ECD-Fc, recombinant human ErbB3/ECD-Fc, recombinant human ErbB4/ECD-Fc or recombinant human Fc in 0.4 ml binding buffer. All solutions were incubated for 2 h at 37° C., followed by incubation with protein G-sepharose beads for 1 h at room temperature. The immunoprecipitates were washed with IP washing buffer and then subjected to western blot analysis. In experiments using whole cell lysates, cells were lysed in M-PER buffer supplemented with a proteinase inhibitor mix (Roche Applied Science), and the lysates were incubated with a specific antibody overnight at 4° C., followed by pull down by protein G-agarose. The immunoprecipitates were washed with IP washing buffer and analyzed by western blotting. To measure the effect of PEPD on PTEN tyrosine phosphorylation, cells were pretreated with 30 μM pervanadate for 10 min to inhibit relevant tyrosine phosphatase and then treated with PEPD or vehicle, followed by preparation of cell lysates for analysis. Pervanadate was prepared fresh by incubating 10 mM vanadate with 10 mM hydrogen peroxide for 15 min at room temperature, followed by addition of catalase (Sigma) at final concentration of 0.2 mg/ml to remove residual hydrogen peroxide.

ELISA-Based Measurement of PEPD and PEPD Binding to ErbB2.

To measure PEPD binding to human ErbB2 or its deletion mutants, ELISA plates were coated overnight at 4° C. with 100 μl/well of an ErbB2 antibody (binding to the cytoplasmic tail of ErbB2) at 10 μg/ml. After washing the wells three times with PBST, residual protein binding sites in the wells were blocked by incubation for 2 h at room temperature with 300 μl/well of 1% BSA in PBS. Following addition of 60 μl of serially diluted recombinant human PEPD into each well, 60 μl of cell lysates (prepared from CHO-K1 cells transfected with the empty vector for 24 h and CHO-K1 cells transfected with wild-type ErbB2 for 24 h), containing 25 μg of total protein per sample (note: a preliminary experiment using up to 250 μg of total protein per sample showed similar outcome of PEPD binding to ErbB2), were added to each well and incubated at 37° C. for 2 h. After three washes with PBST, 100 μl of a biotin-conjugated anti-His antibody (1:10,000 dilution; note that PEPD is His-tagged) was added to each well and incubated for 2 h at room temperature. After another round of washing with PBST, 100 μl of streptavidin-conjugated HRP (1:10,000 dilution) was added to each well and incubated for 45 min at room temperature. After another round of washing with PBST, 100 μl/well of 1× substrate solution (3,3',5,5'-tetramethylbenzidine) was added, and after adequate color development, 100 μl/well of stop solution (1 N $H_2SO_4$) was added and absorbance reading at 450 nm was recorded. In experiments comparing PEPD binding to wild-type ErbB2 and its deletion mutants (deletion of subdomains 1, 2, 3 or 4 in the ErbB2 ECD), an equal amounts of wild-type ErbB2 protein and its mutants were used. The lysates of cells transfected with the plasmid expressing each protein (for 24 h) were first subjected to western blot analysis, followed by densitometry measurement of the specific protein bands normalized to a loading control, to calculate the amount of lysates that deliver the same amount of each protein (25 μg of total protein/sample were used for lysates carrying the wild-type ErbB2).

Measurement of PEPD Concentration by ELISA.

To measure PEPD concentrations, 96-well ELISA plates were coated with 100 μl/well of diluted anti-PEPD mouse monoclonal antibody (2.5 μg/ml) at 4° C. overnight. The plates were then washed three times with phosphate buffered saline with Tween 20 (PBST) and blocked with 200 μl/well of blocking buffer (incubation for at least 2 h at room temperature). The plates were washed with PBST and then incubated with 100 μl/well of PEPD standard or samples, which were appropriately diluted, for 2 h at room temperature. The plates were washed three times with PBST, and each well was then incubated with 100 μl of a detection antibody (an anti-PEPD rabbit polyclonal antibody) for 2 h at room temperature. After washing the plates three times with PBST, 100 μl of secondary reagent (goat-anti-rabbit IgG-HRP) were added to each well, followed by 1 h incubation at room temperature. The plates were washed again with PBST three times, and each well was then incubated with 100 μl of a HRP substrate solution (3,3',5, 5'-tetramethylbenzedine substrate from Cell Signaling, #7004). After adequate color development, 100 μl of stop solution (Cell Signaling, #7002) was added to each well, and absorbance at 450 nm was recorded by a microtiter plate reader. Pure PEPD was used as a standard.

Immunofluorescence Staining and Confocal Microscopy.

Cells were grown in chamber slides ($1.5 \times 10^4$ cells/well) overnight, followed by treatment with PEPD or vehicle. The cells were then washed with ice-cold PBS, fixed with 4% paraformaldehyde for 15 min at room temperature, washed again with ice-cold PBS, and blocked with 1% BSA in PBS for 45 min at room temperature. The cells were then incubated with an ErbB2 antibody for 1 h at room temperature, washed with PBS, incubated with a FITC-conjugated His-tag antibody (for PEPD detection) and a TRITC-conjugated secondary antibody (for ErbB2 detection) for 1 h at room temperature, and washed again with PBS. The cells were then examined with a Zeiss LSM 510 confocal microscope.

RT-PCR.

Total RNA was isolated using the RNeasy Mini Kit (Qiagen), and after treatment with TURBO DNase to remove potential genomic DNA contamination, 500 ng RNA per sample was reverse transcribed into cDNA in 25 μl reaction using the TaqMan Reverse Transcription Reagents (Invitrogen). The RT reaction was performed at 25° C. for 10 min, followed by heating at 48° C. for 30 min, and then 95° C. for 5 min. Each PCR amplification was carried out in 20 μl volume, containing 10 μl GoTaq Master Mix (2×) (Promega), 0.5-1 μl of the reverse-transcribed mixture (cDNA), 0.25 μM each of specific forward and reverse primers. The primers are as follows: human ERBB2, forward, 5'-CTGTTTGCCGTGCCACCCTGAGT-3' (SEQ ID NO:8), reverse, 5'-CTTCTGCTGCCGTCGCTTGATGAG-3' (SEQ ID NO:9); human GAPDH, forward, 5'-CCAGGGCTGCTTTTAACTC-3' (SEQ ID NO:10), reverse, 5'-GCTCCCCCCTGCAAATGA-3' (SEQ ID NO:11); Chinese hamster GAPDH, forward, 5'-TGGAATCTACTGGCGTCTTC-3' (SEQ ID NO:12), reverse, 5'-CACCACCTTCTTGATGTCCT-3' (SEQ ID NO:13). The PCR conditions used for all reactions are as follows: 94° C. for 3 min, 28 cycles (human ERBB2)/25 cycles (GAPDH) at 94° C. (denaturation) for 30 sec, 63° C. (human ERBB2)/60° C. (human GAPDH)/56° C. (Chinese hamster GAPDH) for 30 sec (annealing), and 72° C. for 30 sec (extension); the final extension was performed at 72° C. for 5 min. The PCR products were analyzed by electrophoresis with 1% agarose gel, stained by ethidium bromide, and visualized under UV light.

BrdU Assay.

BrdU incorporation into DNA was measured using the FITC BrdU Flow Kit (BD Pharmingen). Briefly, cells were grown in 6-well plates ($0.15 \times 10^6$ cells/well for CHO-K1 cells and CHO-K1/ErbB2 cells, $0.4 \times 10^6$ cells/well for BT-474 cells; 2 ml medium/well) overnight, treated with vehicle or PEPD for 48 h, and then incubated with BrdU at 10 μM in culture medium for 30 min (CHO-K1 cells and CHO-K1/ErbB2 cells) or 18 h (BT-474 cells). The cells were then harvested, fixed and permeabilized in fixation/permeabilization buffer, treated with NDase for 1 h at 37° C., and incubated with a BrdU antibody for 20 min at room temperature, followed by DNA staining with 7-amino-actinomycin D. The stained cells were resuspended in 0.5-1 ml of staining buffer per sample and analyzed by a flow cytometer (BD FACS Calibur, BD Biosciences), counting 10,000 cells per sample. BrdU incorporation was modeled using the WinMDI 2.8 software.

Soft Agar Colony Formation Assay.

After 1 ml of 0.8% ultrapure Noble Agar (USB, cat#10907) in culture medium was solidified in each well of 6-well plates, 1 ml of cells ($2 \times 10^4$ BT-474 cells, $1 \times 10^3$ CHO-K1 cells or $1 \times 10^3$ CHO-K1/ErbB2 cells) suspended in 0.4% agar in culture medium at 37° C. were added to each well, which also solidified afterwards. PEPD or vehicle was then added in 2 ml of medium to each well, which was changed every 3-4 days for a total of 21 days. At the end of this treatment, cell colonies of ≥100 μm in diameter were counted under a dissection microscope (Axiovert 40 CFL, Carl Zeiss) in 10 different fields (10× magnification) per well, aided by ImageJ.

Cell Invasion and Migration Assay.

Cell invasion and migration were measured using the BD BioCoat Matrigel Invasion Chambers (BD Biosciences). Briefly, the lower chamber was filled with 0.75 ml medium with 10% FBS, and the upper chamber was placed with $4 \times 10^4$ cells suspended in 0.5 ml of serum-free medium containing vehicle or PEPD. The chambers were placed in a cell culture incubator at 37° C. for 48 h. At the end of the incubation, the cells that invaded through a Matrigel matrix layer coated on the filter insert which was placed at the bottom of the invasion chamber were fixed with 100% methanol, stained with 0.5% crystal violet, and counted under a microscope (Eclipse 50i) in 10 different fields (20× magnification) per filter, aided by ImageJ.

PI3 Kinase Assay.

A PI3-Kinase Activity ELISA Kit (Echelon, K-1000s) was used. Briefly, PI3K was pulled down from whole cell lysates (prepared from approximately $1 \times 10^6$ cells per sample) using an PI3K antibody (anti-PI3K p85), and the immunoprecipitates were mixed with 30 μl of KBZ reaction buffer, which was then mixed with 30 μl of 10 μM $PI(4,5)P_2$ substrate, followed by incubation for 2 h at 37° C. The kinase reaction was terminated by adding 90 μl of kinase stop solution to each reaction solution, and 60 μl of each stopped kinase reaction solution was transferred together with 60 μl of $PIP_3$ detector to each well in the incubation plate. After incubation at room temperature for 60 min, 100 μl per sample from the incubation plate was transferred to the corresponding wells of the detection plate and incubated for 60 min at room temperature. The plates were washed with TBST and then incubated with the HRP-conjugated secondary detector for 30 min, followed by washing with TBST, and the immobilized HRP was measured by a standard colorimetric assay, using 3,3',5,5'-tetramethylbenzedine as a substrate.

Src Kinase Assay.

Src activity in cell lysates was measured using the Universal Tyrosine Kinase Assay Kit (TaKaRa, #MK410). Briefly, lysates (prepared from approximately 1×10$^6$ cells per sample) were pre-cleared with protein A-agarose beads prior to IP with a Src antibody. The immunoprecipitates were washed and incubated with 10 mM β-mercaptoethanol in 150 µl of kinase reaction solution. Each sample (40 µl) was mixed with 10 µl of 40 mM ATP-2Na solution, which was transferred to microtiter plate wells coated with a PTK substrate, followed by incubation at 37° C. for 30 min. After wash with TBST, an HRP-conjugated anti-phosphotyrosine (PY20) solution was added to each well and incubated for 30 min at 37° C. After another round of wash with TBST, the immobilized HRP was measured by a standard colorimetric assay, using 3,3',5,5'-tetramethylbenzedine as a substrate.

MTT Cell Proliferation Assay.

Cells were grown in 96-well plates (500 CHO-K1 cells or CHO-K1/ErbB2 cells per well, 2,000 BT-474 cells per well; 150 µl medium per well) overnight and then treated with vehicle, PEPD, G278D-PEPD or trastuzumab in 200 µl medium per well for 72 h, followed by incubation with MTT (9.2 mM in medium) at 37° C. for 3 h. The cells were then washed with PBS and mixed with dimethyl sulfoxide (150 µl per well), and the cell density was determined by measuring the reduction of MTT to formazan spectroscopically at 570 nm.

Statistical Analysis.

Student t-test and ANOVA were used for two-group comparison and multi-group comparison, respectively. All tests were two-sided and performed at a nominal significance level of 0.05, i.e. P value of 0.05 or lower was considered statistically significant.

While the invention has been described through illustrative examples, routine modifications will be apparent to those skilled in the art, which modifications are intended to be within the scope of the invention.

We claim:

1. A method for therapy of ErbB2-positive cancer in an individual, the method comprising selecting an individual for the therapy based on a determination of ErbB-2 positive cancer cells in a sample of a tumor from the individual, and subsequently inhibiting the growth of the tumor by administering to the individual an effective amount of a composition comprising peptidase D (PEPD) comprising a mutation of glycine at position 278 of SEQ ID NO:1, such that growth of the ErbB2-positive tumor is inhibited.

2. The method of claim 1, further comprising administering a coagulation inhibitor to the individual.

3. The method of claim 1, wherein the PEPD is a component of a fusion protein.

4. The method of claim 1 wherein the PEPD is conjugated to a chemotherapeutic agent.

5. The method of claim 1, wherein the mutation of the glycine at position 278 of SEQ ID NO:1 is a G278D mutation.

6. The method of claim 5, further comprising administering a coagulation inhibitor to the individual.

* * * * *